United States Patent
von Blumenthal

(10) Patent No.: US 8,528,552 B2
(45) Date of Patent: Sep. 10, 2013

(54) SPO$_2$ CONTROL WITH ADAPTIVE LINEAR COMPENSATION

(75) Inventor: Tilman von Blumenthal, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 421 days.

(21) Appl. No.: 12/627,428

(22) Filed: Nov. 30, 2009

(65) Prior Publication Data

US 2010/0139659 A1    Jun. 10, 2010

Related U.S. Application Data

(60) Provisional application No. 61/118,927, filed on Dec. 1, 2008, provisional application No. 61/158,451, filed on Mar. 9, 2009.

(30) Foreign Application Priority Data

Mar. 16, 2009   (DE) .......................... 10 2009 013 396

(51) Int. Cl.
*F16K 31/02*   (2006.01)
*A61M 16/16*   (2006.01)

(52) U.S. Cl.
USPC ............ 128/204.21; 128/204.18; 128/203.16; 128/203.17; 128/203.26

(58) Field of Classification Search
USPC ............. 128/200.24, 203.12, 203.14, 203.25, 128/204.18, 204.21, 204.22, 204.23, 204.26, 128/205.11
See application file for complete search history.

(56) References Cited

U.S. PATENT DOCUMENTS

| | | | |
|---|---|---|---|
| 3,734,091 A | 5/1973 | Taplin | |
| 4,286,751 A * | 9/1981 | Fowler | 236/44 R |
| 4,889,116 A | 12/1989 | Taube | |
| 4,928,687 A | 5/1990 | Lampotang et al. | |
| 4,988,946 A | 1/1991 | Kocache et al. | |
| 5,005,573 A | 4/1991 | Buchanan | |
| 5,103,814 A * | 4/1992 | Maher | 128/204.18 |
| 5,116,088 A * | 5/1992 | Bird | 285/319 |
| 5,205,281 A | 4/1993 | Buchanan | |
| 5,282,464 A | 2/1994 | Brain | |
| 5,299,579 A | 4/1994 | Gedeon et al. | |
| 5,315,990 A | 5/1994 | Mondry | |
| 5,335,659 A | 8/1994 | Pologe | |
| 5,353,788 A | 10/1994 | Miles | |

(Continued)

FOREIGN PATENT DOCUMENTS

| | | |
|---|---|---|
| DE | 4309923 C2 | 9/1994 |
| EP | 0504725 A3 | 9/1992 |

(Continued)

*Primary Examiner* — Justine Yu
*Assistant Examiner* — Michael Tsai
(74) *Attorney, Agent, or Firm* — McGlew and Tuttle, P.C.

(57) ABSTRACT

A device and a process for controlling a respirator with inclusion of an oxygen saturation value (34) for compensating a device-dependent time response (15), a physiological time response (16) and a measuring method-dependent time response (17) are described. The device-dependent time response (15), the physiological time response (16) and the measuring method-dependent time response (17) are determined in a continuous sequence and a run time of a change in the oxygen concentration from the metering means (9) in the respirator to the patient (4) is determined and taken into account in regulating the oxygen concentration.

30 Claims, 10 Drawing Sheets

(56) References Cited

U.S. PATENT DOCUMENTS

| | | | |
|---|---|---|---|
| 5,365,922 A * | 11/1994 | Raemer | 128/204.23 |
| 5,388,575 A | 2/1995 | Taube | |
| 5,396,882 A | 3/1995 | Zapol | |
| 5,429,123 A | 7/1995 | Shaffer et al. | |
| 5,485,850 A | 1/1996 | Dietz | |
| 5,520,192 A | 5/1996 | Kitney et al. | |
| 5,647,345 A | 7/1997 | Saul | |
| 5,676,133 A | 10/1997 | Hickle et al. | |
| 5,682,877 A * | 11/1997 | Mondry | 128/204.23 |
| 5,743,253 A * | 4/1998 | Castor et al. | 128/200.24 |
| 5,752,509 A | 5/1998 | Lachmann et al. | |
| 5,799,652 A | 9/1998 | Kotliar | |
| 5,826,579 A | 10/1998 | Remmers et al. | |
| 5,827,415 A | 10/1998 | Gur et al. | |
| 5,954,050 A | 9/1999 | Christopher | |
| 5,975,081 A | 11/1999 | Hood et al. | |
| 6,123,072 A | 9/2000 | Downs | |
| 6,142,149 A | 11/2000 | Steen | |
| 6,148,814 A | 11/2000 | Clemmer et al. | |
| 6,186,142 B1 | 2/2001 | Schmidt et al. | |
| 6,199,550 B1 | 3/2001 | Wiesmann et al. | |
| 6,253,098 B1 | 6/2001 | Walker et al. | |
| 6,269,679 B1 * | 8/2001 | McCarthy et al. | 73/19.1 |
| 6,283,123 B1 | 9/2001 | Van Meter et al. | |
| 6,314,956 B1 | 11/2001 | Stamler et al. | |
| 6,327,497 B1 | 12/2001 | Kirchgeorg et al. | |
| 6,334,065 B1 | 12/2001 | Al-Ali et al. | |
| 6,371,112 B1 | 4/2002 | Bibi | |
| 6,371,114 B1 | 4/2002 | Schmidt et al. | |
| 6,381,479 B1 | 4/2002 | Norris | |
| 6,413,226 B1 | 7/2002 | Starr et al. | |
| 6,470,885 B1 | 10/2002 | Blue et al. | |
| 6,512,938 B2 | 1/2003 | Claure et al. | |
| 6,526,297 B1 | 2/2003 | Merilainen | |
| 6,532,958 B1 | 3/2003 | Buan et al. | |
| 6,557,553 B1 | 5/2003 | Borrello | |
| 6,560,470 B1 | 5/2003 | Pologe | |
| 6,561,193 B1 | 5/2003 | Noble | |
| 6,579,592 B1 | 6/2003 | Matsubaguchi et al. | |
| 6,632,402 B2 | 10/2003 | Blazewicz et al. | |
| 6,644,312 B2 | 11/2003 | Berthon-Jones et al. | |
| 6,671,529 B2 | 12/2003 | Claure et al. | |
| 6,761,165 B2 * | 7/2004 | Strickland, Jr. | 128/204.22 |
| 6,796,305 B1 | 9/2004 | Banner et al. | |
| 6,811,538 B2 | 11/2004 | Westbrook et al. | |
| 6,832,609 B2 | 12/2004 | Wright et al. | |
| 6,848,444 B2 | 2/2005 | Smith et al. | |
| 6,871,645 B2 | 3/2005 | Wartman et al. | |
| 6,874,500 B2 | 4/2005 | Fukunaga et al. | |
| 6,935,339 B2 | 8/2005 | Mattar Neto et al. | |
| 7,008,380 B1 | 3/2006 | Rees et al. | |
| 7,013,898 B2 | 3/2006 | Rashad et al. | |
| 7,222,624 B2 | 5/2007 | Rashad et al. | |
| 7,246,620 B2 | 7/2007 | Conroy, Jr. | |
| 7,308,894 B2 | 12/2007 | Hickle | |
| 7,527,054 B2 * | 5/2009 | Misholi | 128/204.22 |
| 2001/0029325 A1 | 10/2001 | Parker | |
| 2002/0072659 A1 * | 6/2002 | Claure et al. | 600/323 |
| 2002/0139368 A1 | 10/2002 | Bachinski | |
| 2002/0177762 A1 | 11/2002 | Norris et al. | |
| 2005/0066970 A1 | 3/2005 | Donofrio | |
| 2005/0113709 A1 | 5/2005 | Millet | |
| 2006/0060198 A1 | 3/2006 | Aylsworth et al. | |
| 2006/0225737 A1 | 10/2006 | Iobbi | |
| 2006/0266355 A1 | 11/2006 | Misholi | |
| 2008/0006271 A1 | 1/2008 | Aylsworth et al. | |
| 2008/0053438 A1 | 3/2008 | DeVries et al. | |
| 2008/0066752 A1 * | 3/2008 | Baker et al. | 128/204.23 |
| 2008/0066753 A1 | 3/2008 | Martin et al. | |
| 2008/0072906 A1 | 3/2008 | Starr et al. | |
| 2008/0188733 A1 * | 8/2008 | Al-Ali et al. | 600/364 |
| 2008/0314385 A1 | 12/2008 | Brunner et al. | |

FOREIGN PATENT DOCUMENTS

| | | |
|---|---|---|
| EP | 0973443 B1 | 1/2000 |
| EP | 0998318 B1 | 5/2000 |
| EP | 1245250 A3 | 10/2002 |
| EP | 1579883 A2 | 9/2005 |
| JP | 6197968 A | 7/1994 |
| WO | WO9829034 A1 | 7/1998 |
| WO | WO 9904841 | 2/1999 |
| WO | WO03038566 A2 | 5/2003 |
| WO | WO03082390 A1 | 10/2003 |
| WO | WO03084454 A2 | 10/2003 |
| WO | WO2004030525 A2 | 4/2004 |
| WO | WO2004058351 A1 | 7/2004 |
| WO | WO2004089212 A1 | 10/2004 |
| WO | WO2004093770 A2 | 11/2004 |
| WO | WO2005013879 A2 | 2/2005 |
| WO | WO2005051280 A2 | 6/2005 |
| WO | WO2006014399 A2 | 2/2006 |
| WO | WO2007085108 A1 | 8/2007 |

* cited by examiner

SPO$_2$ CONTROL WITH ADAPTIVE LINEAR COMPENSATION

CROSS REFERENCE TO RELATED APPLICATIONS

This application claims the benefit of priority under 35 U.S.C. §119 of German Patent Application 10 2009 013 396.8 filed Mar. 16, 2009. This application also claims the benefit of priority under 35 U.S.C. §120 of U.S. Provisional Application No. 61/118,927 filed Dec. 1, 2008 and U.S. Provisional Application No. 61/158,451 filed Mar. 9, 2009. The entire contents of each application are incorporated herein by reference.

FIELD OF THE INVENTION

The present invention pertains to a device and a process for controlling the metering of oxygen in a respirator.

BACKGROUND OF THE INVENTION

It is necessary to monitor the metering of oxygen in the blood during the mechanical respiration of patients, especially newborn and premature babies. A physiologically unadapted saturation, which is subject to great variations in terms of the degree of saturation, may lead to damage to the eyes with the negative consequence of partial or total blindness (retinopathy of premature: ROP) in case of an oxygen concentration of 98% to 100% in the blood lasting over a period of several minutes. Other side effects of a highly fluctuating oxygen concentration are permanent lung injury (ALI (acute lung injury)) as well as brain damage. The selection of the oxygen concentration combined with the other parameters of respiration such as respiration rate and minute volume are decisive for a physiologically correct respiration in adults as well; this means that the combination of the parameters set must be selected to be such that the carbon dioxide is removed from the patient's lungs by the gas exchange, such that the carbon dioxide is replaced by a correspondingly selected quantity of oxygen in the course of respiration. To ensure the respiration parameters, a blood gas analysis is performed in the clinical routine after connection to the respirator for the first rime and after operation with starting parameters. A blood sample is taken for this from the patient according to an invasive method and the oxygen and carbon dioxide concentrations are determined from the sample.

Continuous monitoring of the oxygen concentration (SaO$_2$) by means of taking blood samples is not possible in clinical practice, and the oxygen saturation (SPO$_2$) is available for a continuous monitoring. The measurement of the oxygen saturation (SPO$_2$) is performed in a suitable manner by means of a pulse oximeter. The oxygen saturation is determined during such a measurement in a noninvasive manner according to the optical transillumination method on the extremities or on the ear lobe by means of suitable finger sensors or ear lobe sensors adapted to the site of measurement. A suitable pulse oximetric sensor is shown in US 2001029325A. The measurement is carried out by means of a mutual transillumination, for example, of the finger, using two wavelengths in the red and infrared ranges. Measuring arrangements designed in this manner are shown in US 2002177762 A, US 2008188733 A and U.S. Pat. No. 6,381,479 B. Besides the oxygen saturation, these pulse oximeters detect the heart rate as another measured variable. Typical sampling rates of such devices are in the range of 0.1 Hz to 2 Hz. To reliably maintain the oxygen saturation at a physiologically adapted level, the inspiratory oxygen fraction (FiO$_2$) is very often adjusted manually during respiration on the respirator in clinical practice. Inclusion of values of an oxygen saturation in the blood to determine a suitable inspiratory oxygen fraction (FiO$_2$) in the breathing air is described in the state of the art; for example, U.S. Pat. No. 4,889,116 describes an adjustment of FiO$_2$ in a predetermined target range of the oxygen saturation. The arterial oxygen saturation SaO$_2$ is used in U.S. Pat. No. 5,388,575 A as a calculated and estimated auxiliary variable in connection with a linear interpolation of the nonlinearity of the SPO$_2$—SaO$_2$ curve in order to move physiologically closer to the target range of FiO$_2$ from the measured SPO$_2$ value. The use of the past history of the oxygen saturation values by means of trend analysis is known from U.S. Pat. No. 5,388,575 A, U.S. Pat. No. 6,512,938 B2 and U.S. Pat. No. 6,761,165 B2. U.S. Pat. No. 5,365,922 describes a closed control loop with the use of an SPO$_2$ sensor and a measuring device in the feedback of the control loop. Adjustment of the oxygen concentration leads to a response of the oxygen saturation only after a time lag in the closed control loop. Since the time lags depend on both the measuring arrangement, the type of gas metering and gas supply to the patient and the physiological and pathological constitution of the patient, designing the controller for a physiological and pathological patient constitution may lead to an unstable control characteristic, whereas the equivalent design of the controller for another physiological and pathological patient constitution leads to a response time of oxygen metering that is not acceptable from a physiological and therapeutic point of view or to an unacceptable permanent deviation of the oxygen saturation in the blood compared to a target range. U.S. Pat. No. 5,682,877 describes the inclusion of the oxygen saturation in the control loop of oxygen metering, in which time lags concerning the process of oxygen metering over time in the device between an SPO$_2$ measuring site, arranged, for example, on the upper and lower extremities, and the lungs, as well as possible times, which are necessary for obtaining stable measuring conditions after a change in metering, and preset waiting times in the serial process of oxygen regulation and oxygen metering are also taken into account.

The assignment of a saturation value to a discrete state of the patient, e.g., hypoxia, and the use of this state as an input variable for the adjustment characteristic of the oxygen fraction FiO$_2$, is likewise described in U.S. Pat. No. 6,512,938 B2. An improvement of oxygen metering, associated with a reduced fluctuation of the oxygen concentration in the blood, can be achieved with U.S. Pat. No. 6,512,938 B2 for a limited number of patients, whose clinical pictures are classified. For a closed control loop, using an SPO$_2$ sensor, US 2008/0066752 A1 describes the taking into account of physiological time lags in the control loop in adjusting the oxygen metering in order to reduce the range of variation of the oxygen concentration.

It is necessary to take into account additional factors to further reduce the variation in the oxygen concentration.

SUMMARY OF THE INVENTION

The object of the present invention is to propose a process and a device for obtaining a uniform blood gas oxygen concentration.

The object is accomplished according to the present invention with respect to the process for obtaining a uniform blood gas oxygen concentration. The respirator comprises a control and calculating unit, a gas path, a gas-mixing unit, a gas-metering unit, a measuring arrangement for measuring an oxygen saturation, an input unit and a controller. At least one time function element is provided. One or more time responses of the respirator are simulated for the measuring arrangement for measuring an oxygen saturation and a patient in the at least one time function element. A set value of an oxygen concentration in the respirator is provided. A saturation-effective oxygen concentration is determined from the set value of the oxygen concentration in the respirator and a curve of the set value and the at least one time function element. A measured value of a current oxygen saturation is determined. A set point of an oxygen saturation is provided to the respirator. A difference value of an oxygen concentration is determined from the set point of the oxygen saturation and the measured value of the current oxygen saturation. The difference value of the oxygen concentration is linked with the saturation-effective oxygen concentration to form an updated set value of the oxygen concentration and a metering of the oxygen concentration in the respirator is set based on the updated set value of the oxygen concentration.

A process is provided for controlling a respirator. At least one time function element is provided. At least one time response of the respirator, the humidifying unit, the measuring arrangement for the oxygen saturation measurement or a patient is simulated in the at least one time function element. A set value of an oxygen concentration is provided to the respirator. A saturation-effective oxygen concentration is determined based on the set value of the oxygen concentration in the respirator and a curve of the set value and the at least one time function element. A measured value of a current oxygen saturation is determined. A set point of an oxygen saturation is provided to the respirator. A difference value of the oxygen concentration is determined based on the set point of the oxygen saturation and the measured value of the current oxygen saturation. The difference value of the oxygen concentration and the saturation-effective oxygen concentration are linked to a new set value of the oxygen concentration and a metering of the oxygen concentration of the respirator is set based on the new set value of the oxygen concentration.

A process is provided for controlling a respirator. A respirator is provided comprising an expiration valve, a control and calculating unit, an input unit, a controller, a gas path with a Y-piece, a gas-mixing unit and a gas-metering unit. The respirator comprises a control loop for setting an oxygen saturation corresponding to a preset set value at a patient, wherein the control loop comprises a measuring component. The measuring component comprises a measuring arrangement for measuring an oxygen saturation. The control loop comprises a modeling element, wherein the modeling element comprises a first time lag element with a device-dependent time response. An oxygen concentration value is calculated at the Y-piece and a saturation-effective oxygen concentration based on the device-dependent time response. The saturation-effective oxygen concentration is additively linked with an output of the controller via a feedback and a summation signal is sent as output to the gas-metering unit and to the modeling element.

A process is provided for controlling a respirator. A respirator is provided. The respirator comprises an expiration valve, a control and calculating unit, a controller, an input unit, a gas path with a Y-piece, a gas-mixing unit and a gas-metering unit. The control and calculating unit comprises a control loop for setting an oxygen saturation corresponding to a preset set value at a patient, wherein the control loop comprises a measuring component. The measuring component comprises an oxygen saturation sensor and an oxygen saturation-measuring unit, said control loop comprising a modeling element. The modeling element comprises a first time lag element with a device-dependent time response, a second time lag element with a patient-dependent time response and a third time lag element with a time response dependent on the measuring method. An oxygen concentration value is calculated at the Y-piece and a saturation-effective oxygen concentration based on the device-dependent time response, the patient-dependent time response and the measuring method-dependent time response. The saturation-effective oxygen concentration is linked with an output of the controller via a feedback and a summation signal is sent to the gas-metering unit and to the modeling element.

At least one time lag element may comprise a second time lag element and a third time lag element. The second time lag element may simulate the time response of the oxygen transport from the inspired air into the blood circulation. The third time lag element may simulate the time response of the measuring arrangement.

The modeling of the time response of the oxygen transport from the inspired air into the blood circulation and of the measuring method-dependent time response of the measuring arrangement used to measure the oxygen saturation may be combined in a fourth process step with the simulation of the device-dependent time response in a common time response.

The device-dependent time response may comprise a time response of a humidifying unit.

Each of the time lag elements may have one or more of a first-order time function element and a time function element in a series connection.

The set value of the oxygen concentration may be complemented by a measured value of the oxygen concentration.

The set of measured oxygen saturation values may be taken into account in a modeling of a patient's time response.

A measured value of a heart rate may be taken into account in a modeling of a patient's time response.

A quality index of the set of oxygen saturation measured values and of the measured value of the heart rate may be taken into account in modeling the patient's time response.

The time curve of the set value of the oxygen concentration may be compared with a time curve of the measured value of the oxygen saturation and the modeling of the one or more time responses may be changed based the time curve comparison.

A frequency response of the set value of the oxygen concentration may be compared with a frequency response of the measured value of the oxygen saturation and modeling of the one or more time responses may be changed based on the frequency response comparison.

A quality index of the measured oxygen saturation values may be sent to the control and regulating unit and the measured value of the oxygen saturation may be changed based on the quality index of the set of measured values.

According to another aspect of the invention, a device is provided for controlling a respirator that comprises an expiration valve, a control and calculating unit, an input unit, a gas path with a Y-piece, a gas-mixing unit and a gas-metering unit. The device comprises a control loop for setting an oxygen saturation corresponding to a preset set value at a patient, wherein the control loop comprises a measuring component. The measuring component comprises a measuring arrangement for measuring an oxygen saturation. The control loop comprises a modeling element, wherein the modeling element comprises a first time lag element with a device-dependent time response. The control loop comprises a controller. The controller provides a controller output signal as output, wherein the modeling element is connected to the controller output signal via a feedback. The device-dependent time response and the controller output signal forming a summation signal. The summation signal is sent to the modeling element as an input variable and to the gas-metering unit as a set value of the oxygen concentration. The gas-metering unit sets an oxygen concentration in the breathing gas of patient based on the set value.

According to another aspect of the invention, a device is provided for controlling a respirator. The respirator comprises an expiration valve, a control and calculating unit, an input unit, a gas path with a Y-piece, a gas-mixing unit and a gas-metering unit. The device comprises a control loop for setting an oxygen saturation corresponding to a preset set value at a patient, wherein the control loop comprises a measuring component. The measuring component comprises an oxygen saturation sensor and an oxygen saturation-measuring unit. The control loop comprises a modeling element and a controller. The controller provides a controller output signal as output, wherein the modeling element comprises a first time lag element with a device-dependent time response, a second time lag element with a patient-dependent time response and a third time lag element with a time response dependent upon a measuring method. The modeling element is connected to the controller output signal via a feedback, wherein output from the modeling element and the controller output signal form a summation signal. The summation signal is sent as an input variable to the modeling element and to the gas-metering unit as a set value of an oxygen concentration. The gas-metering unit sets an oxygen concentration in the breathing gas of patient based on the set value.

Each of the time lag elements may have a first-order time function element and a dead time function element in a series connection.

A humidifying unit may be contained in the gas path from the respirator to the patient and the modeling element may include the humidifying unit in the first time lag element with the device-dependent time response.

A set of measured oxygen saturation values may be sent to the second time lag element.

A measured value of a heart rate may be sent to the second time lag element.

A quality index of the set of measured oxygen saturation values and of the measured value of the heart rate may be sent to the second time lag element.

A quality index of the set of measured oxygen saturation values may be sent to the control and calculating unit and the measured value of the oxygen saturation may be changed corresponding to the quality index of the set of measured values.

A humidifying unit may be arranged during inspiration in the gas path leading to the patient, wherein the humidifying unit may be taken into account in the modeling element in the first time lag element.

The device and process may be used to respirate at least one premature or newborn child with the respirator such that damage to the eyes of the premature or newborn child and total or partial blindness of the premature or newborn child are prevented.

The device and process may be used to respirate children, youth and adults with the respirator such that hypoxic states of patients are prevented.

The device and process may be used to respirate patients in an adverse medical care situation with the respirator.

The time lags of the measuring arrangement, of the type of gas metering and gas supply and gas distribution up to the patient are reduced according to the present invention by determining an oxygen concentration at the patient on the basis of the run times of a change in the oxygen concentration in the gas mixture being metered up to the patient, which said change is brought about by the gas metering.

The determination of the run times and time lags of the change in the oxygen concentration is performed according to the present invention by an estimation from the measured variables and characteristics of the measuring arrangement comprising the patient, respirator and oxygen saturation-measuring means and by an analysis of a measured value of the oxygen saturation in the blood after a change that took place previously in the metering of the oxygen concentration in the respiration circuit. The run times and time lags of the change in the oxygen concentration are also included according to the present invention by means of a feedback of a blood oxygen concentration into the oxygen metering control loop of a respirator. The blood oxygen concentration is measured by pulse oximetry as an oxygen saturation value $SPO_2$. The effect of the transfer function between the oxygen of the air made available, the exchange of oxygen of the air with blood oxygen in the lung and the measured oxygen saturation in the blood is also included by this feedback of the oxygen saturation value into the control loop of the oxygen-metering means. The tendency of the oxygen saturation to overshoot in the control loop is thus reduced without reducing the response rate of the controller to changes in saturation. The control performance of the oxygen saturation control is increased and an improvement in the uniformity of the blood gas oxygen concentration is achieved.

The time response of the $SPO_2$ measurement, which depends on the measuring design, the time response of the gas exchange from the lungs into the patient's blood circulation and the time response of the gas and oxygen metering in the respirator, which is determined by the device, including the pneumatic connection to the patient, are summarily also included in the control loop at the output of the controller by modeling these time responses. The knowledge of the properties of the measuring design of the $SPO_2$ measurement combined with the knowledge of the air-to-blood exchange in the patient's lungs and combined with the knowledge of the properties of the respirator are integrated by data networking of the respirator with the oxygen saturation-measuring means and with other accessories, for example, a breathing gas humidifier, and used for modeling.

The inclusion of the time models in the control loop results in a further improvement in the uniformity of the blood gas oxygen concentration.

A respirator comprises actuators, such as air and oxygen metering means; sensors, such as flow, pressure and temperature sensors; control elements, and a user interface. The settings on the respirator are performed via the user interface and arise from the therapeutic considerations of the user, taking the patient's constitution into account, and are used as starting conditions for the oxygen metering means and the selection of the respiration parameters for the patient by the respirator. The air-oxygen mixture being metered is fed to the patient from the respirator via a feed system, preferably a breathing tube system, during inspiration, taking the respiration parameters into account.

The quantity of breathing gas is metered to the patient in the proven manner by an inspiration valve, which is controlled by the process of the respiration cycle. One variant of this type is the control of the quantity of air of a blower, for example, of a radial flow fan, whose speed is varied in the course of the breathing cycle. In addition, a unit for heating and humidification may be arranged in the tube system. The humidifying unit adds water vapor to the breathing air and brings the breathing air into the physiologically favorable climatic range and is used to prevent the patient's respiratory tract from drying and cooling. The humidification is preferably used combined with heatable breathing tubes in order to prevent condensation of the humidified air. An $SPO_2$ sensor is arranged at the finger or at the ear lobe of a patient and is connected to an $SPO_2$ monitor. The $SPO_2$ monitor is connected to a control and calculating unit in the respirator. The measured value of the oxygen saturation is used in the respirator to influence the metering of oxygen. The $SPO_2$ sensor, $SPO_2$ monitor, control and calculating unit and the gas-mixing and gas-metering unit are arranged in a closed control loop. The goal of control is to apply to the patient a quantity of oxygen that is determined in terms of quantity and duration in time such that the $SPO_2$ value determined will be maintained within a predetermined range with the smallest possible deviations. The measuring component of the control loop comprises an $SPO_2$ sensor and $SPO_2$ monitor and the signal input of the control and calculating unit. An input data set, comprising a set point of the oxygen saturation ($SPO_{2\_Soll}$) and a measured value of the oxygen saturation ($SPO_{2\_Ist}$), is sent to the controller. Corresponding to the functionality and the control characteristic of the controller, a difference of the breathing gas oxygen concentration ($\Delta FiO_2$), which will be transferred to the controlled system and sent by the respirator to the patient as a breathing gas being metered corresponding to the control via the air- and oxygen-metering means, is obtained at the output of the controller. The controller is designed as a digital controller, preferably as a controller with a proportionally acting controller part, with an integrally acting controller part and with a differentially acting controller part, as a so-called PID controller, as a part of the control and calculating unit. The digital controller can be described by mathematical relationships or sets of equations and embodied in the digital controller procedure or the control characteristic may be in the form of look-up tables. The look-up tables make possible a conversion from a set of input data, comprising the set point of the oxygen saturation ($SPO_{2\_Soll}$) and the measured value of the oxygen saturation ($SPO_{2\_Ist}$), into a difference value of the breathing gas oxygen concentration ($\Delta FiO_2$). Variants of the look-up table, which also contain a difference value of the oxygen saturation ($\Delta SPO_2$) as a component and/or interim result, are also covered here in the sense of the present invention. In the sense of the present invention, the term PID controller also covers controller characteristics that act predominantly or exclusively proportionally, integrally, proportionally-integrally, proportionally-differentially or differentially. A controller with a controller transfer function that is defined in sections is also covered under the term of a predominantly proportionally, integrally, proportionally-integrally, proportionally-differentially or differentially acting control characteristic. The control loop comprises essentially a controller, a controlled system, a measuring component, a first summation point at the input of the controller, a second summation point at the output of the controller, and a modeling element, which simulates the time response of the arrangement comprising the respirator, the patient being respirated and the $SPO_2$-measuring means. The modeling element is connected to the controlled system as a feedback via the second summation point at the output of the controller and thus affects the regulation of the oxygen concentration. On the one hand, the current set value of the oxygen concentration is sent as input variables to the modeling element, other input variables being the configurations, setting parameters, measured values and data of the respirator and of the $SPO_2$-measuring means. The inclusion of the input variables in the modeling element and the feedback to the output of the controller may be performed unweighted or weighted. Weighting may be designed as an amplifying weighting or as an attenuating weighting. The modeling element is composed of a plurality of time lag elements, which are present in the controlled system and it takes this controlled system into account. On the one hand, the modeling element comprises a volume percent V1 in the gas-mixing and gas-metering unit and the tube connection system within the respirator. A volume V2 of the inspiratory breathing tube system and a volume of the humidifying unit form another part. The volume of the so-called Y-piece directly at the patient, which represents the connection site comprising the inspiratory air supply and the expiratory air discharge in the respiration circuit, is also covered by the volume of the inspiratory breathing tube system in the sense of the present invention. Furthermore, the inspiratory breathing tube system also covers in the sense of the present invention a flow sensor located near the patient, which is arranged at the Y-piece or is integrated in the Y-piece. A third volume percent V3 is obtained from the volume of the humidifying unit. Another part of the modeling element is [composed] of a volume V4 of the bronchial area and the lungs of the patient. These three volume percents V1, V2, V3 can be combined into a total volume $V_{Sum}$ and define a first time lag interval D1 determined by the pneumatic conditions, beginning from the metering of the quantity of oxygen in the respirator and into the patient's lungs. The time lag interval, the time lag elements and the term time lag are defined in the sense of the present invention both as a first-order time function element (PT-1) or time function elements of a higher order (PT-2, PT3-, PT-4) and as a dead time function element (Tt).

This first time lag D1 can be determined in advance summarily for the volumes V1, V2, V3 and also partially for each volume V1, V2, V3 in the knowledge of the orders of magnitude of the flow rate, volumes V1, V2, V3 and the pneumatic resistances corresponding to the four volumes for the metering range of the respirator. Another part of the modeling element results from a volume V4 of the bronchial area and the lungs of the patient. The time lag caused by this volume V4 is also included in a second time lag D2 and is obtained essentially from the physiological and pathological constitution of the patient. Furthermore, D2 is defined as the time lags that are due to the size of the air exchange surface area and the number of alveoli actively participating in the air-blood exchange within the bronchial area and the lungs of the patient, and other factors are possible pathological restrictions of the air exchange or narrowing in the bronchial area (obstructions). A third time lag interval D3 arises from the distribution of the oxygen molecules taken up into the arterial blood via the alveoli and the transport path through the arteries to the site of measurement at the finger or ear lobe of the patient. The transport paths and the resulting transport times for the arterial oxygen are different for the legs, fingers and ear lobe. Another time lag interval and a scaling effect are caused by the relationship between the arterial oxygen concentration and the oxygen saturation, which can be described in the form of the $SPO_2$—$SaO_2$ characteristic. The effect of this time lag cannot be distinguished from that of the time lag D3 caused by the transport and can be considered to be a negligible variable compared to the time D3 caused by the transport and can also be included in the time lag interval D3. A fourth time lag interval D4 results from the principle of measurement of the $SPO_2$ sensor used, as the transillumination principle with optical radiator and red or infrared optical detector opposite it has a different measurement characteristic in time than an arrangement operating according to the reflection principle, where the optical radiator and the red and infrared optical detector are arranged on the same side, for example, of the finger.

This time lag interval is a sensor-specific parameter. $SPO_2$ data logging can be mentioned as the fifth time lag interval. This includes summarily both the optical detection time of the $SPO_2$ sensor-monitor arrangement and the signal detection, signal sampling and signal processing with measured value filtering, artifact and noise signal suppression and digital sampling of the $SPO_2$ monitor, as well as the data transmission rate from the $SPO_2$ monitor to the control and calculating unit of the respirator.

The process according to the present invention reduces the range of variation of the oxygen saturation in the blood in the control loop by continuously taking into account the time lags D1, D2, D3, D4, D5 contained in the controlled system and the changes thereof during the respiration operation.

A sequence of 8 steps specifically illustrates the process according to the present invention for controlling the metering of oxygen in a respirator. The process takes the following course, which is shown in the continuous sequence of steps a) through h):

a) A time response dependent on the device is determined in a first step and is simulated in at least one first time lag element, b) a run time of a change in the oxygen concentration from a metering means in the respirator to the patient is determined in a second step from a set value and a curve of the set value of the oxygen concentration and the at least first time lag element, and a patient-side oxygen concentration is calculated, c) an oxygen saturation measurement is performed with the measuring arrangement in a third step and a set of measured values of the oxygen saturation is determined, d) a time response, which depends on a time response of the oxygen transport from the inspired air into the blood circulation, and a measuring time response, which depends on the measuring arrangement used to measure the oxygen saturation, are determined in a fourth step and simulated in at least one fourth time lag element, e) a saturation-effective oxygen concentration is determined in a fifth step from the patient-side oxygen concentration and the at least first and at least fourth time lag element, f) a difference value is formed in a sixth step from the set of measured values of the oxygen saturation and a set point of the oxygen saturation, g) the controller generates a breathing gas oxygen concentration from the difference value in a seventh step of the process, and h) the blood gas oxygen concentration is linked in an eighth step with the saturation-effective oxygen concentration into a set value of the oxygen concentration, the set value of the oxygen concentration is transmitted to a gas-metering unit, and the gas-metering unit corrects the oxygen concentration.

The process then jumps back to the first step a) and is continuously continued.

The individual steps of the process according to the present invention for controlling the metering of oxygen in a respirator will be described in more detail below.

After the start of the process, the time response dependent on the device is determined in a first step of the process and simulated in a model. The device-dependent time response D1 is obtained from the volumes involved: V1 (respirator), V2 (breathing tube system), V3 (humidifying unit). The time lag D1 is split into a first dead time $Tt_1$, and a first first-order time function element (PT-1) with the time constant $\tau_1$. A control and calculating unit determines a dead time $Tt_1$ and a first time constant $\tau_1$ from V1, V2, V3. The device-dependent time lag D1 is in a range of 3 sec to 20 sec.

The time span of the device-dependent time lag D1 is determined by the arrangement and the properties of the components in the respiration circuit, comprising the respirator with the gas-metering means and respiration control, breathing tube system with the diameter and length configuration, resulting in the pneumatic properties resistance and compliance, other accessories, such as the accessory for humidifying and tempering the breathing gas, and the flow and/or carbon dioxide sensor system near the patient, likewise resulting in the particular pneumatic properties resistance, compliance and dead volume.

Taking the set value of the oxygen concentration in the respirator and the curve of the set value of the oxygen concentration, the first dead time $Tt_1$ and the first time constant $\tau_1$ into account, the pneumatic run time of a change in the oxygen concentration from the metering in the respirator to the Y-piece is determined in the second step of the process and the oxygen concentration present at this point in time is determined.

The inclusion of a curve of a set value or of a curve of a set value comprises in the sense of the present invention the technical and mathematical possibilities of averaging values, for example, the formation of an arithmetic mean, root mean square or sliding averaging over preset time intervals. The set point curve is averaged in a practical embodiment by means of low-pass filtration over a typical time span of 3-10 sec or the set value curve is formed by forming the arithmetic mean or root mean square with a fixed number of measured values of, for example, 100 values in a typical measuring interval of 5 sec or by sliding averaging over a measuring interval of 5 sec to 10 sec. This breathing gas oxygen concentration at the Y-piece is sent in the further course of the process in the fifth step to the time models for taking into account the time lags D2 and D3 that are due to the oxygen transport from the inspired air into the blood circulation and the time lags D4 and D5 due to the measuring method as an input variable. This input variable of the oxygen concentration may be sent unweighted or weighted. Weighting may be either amplifying or attenuating.

The oxygen saturation measurement is performed in a third step of the process by the $SPO_2$ monitor by means of an $SPO_2$ sensor connected to said monitor and a set of measured $SPO_2$ values is transmitted to the control and regulating unit of the respirator. The set of measured $SPO_2$ values is sent as a controlled variable to the input of a controller for metering the breathing gas oxygen concentration. The set of measured $SPO_2$ values receives, on the one hand, a value of the measured oxygen saturation, but additionally also a measured value of the heart rate and, in many practical applications, an index, which indicates the quality of the measured values. The set of measured $SPO_2$ values is sent, moreover, in the further course of the process in the fifth step as a second input variable to the time models for taking into account the time lags D2 and D3 that are due to the oxygen transport from the inspired air into the blood circulation and the time lags D4 and D5 that are due to the measuring method as an input variable. This input variable of the measured $SPO_2$ value, the heart rate and the quality index of the set of measured values may be sent unweighted or weighted. Weighting may be either amplifying or attenuating. The set of measured $SPO_2$ values is sent, furthermore, as a set point for a variance comparison of the oxygen saturation in the sixth step of the process.

The time response due to the oxygen transport from the air in the lungs into the blood circulation is determined in the fourth step of the process and a time response of the oxygen saturation measurement, which depends on the measuring method, is determined and simulated in a model.

These time lags D2 and D3, which are due to the oxygen transport from the inspired air into the blood circulation and will also be called physiological time lags in the further course of the present invention, are imaged by a common time model in the fourth step of the process and are split into a second dead time $Tt_2$ and a second first-order time function element (PT-1) with the time constant $\tau_2$. The physiological time lags D2 and D3 are in a range from less than 10 sec to values of 3 minutes to 5 minutes.

The time span of the physiological time lags D2 and D3 is determined by the age, sex, constitution and clinical picture of the patient. A perfusion disorder, e.g., PPHN (persistent pulmonary hypertension of newborn), may lead to a high value of the physiological time lags, equaling about 5 minutes. The physiological time lag in a healthy newborn is in the range of a few sec and that of adults is in the range of about 10 sec. The time lags D4 and D5 due to the measuring method are imaged in the fourth step of the process by a common time model and are split into a third dead time $Tt_3$ and a third first-order time function element (PT-1) with the time constant $\tau_3$. The time lags D4 and D5 due to the measuring method are typically in a range from at least about 1 sec to a maximum of 20 sec, depending on the design of signal sampling, signal processing and the data transmission being used.

The time span of the time lags D4 and D5 due to the measuring method is determined by the measuring arrangement. The duration and type of data logging from the overall configuration, comprising the dynamic response of the $SPO_2$ sensor, sampling frequency, signal processing, signal amplification and signal filtration, data transmission method, data interface, transmission protocol and transmission rate, are included in the time model.

The effective breathing gas oxygen concentration, which has brought about the effective, currently measured oxygen saturation, is determined in a fifth step of the process from the breathing gas oxygen concentration at the Y-piece (from the second step) as a first input variable and with the set of measured $SPO_2$ values (from the third step) as a second input variable, taking into account the physiological time lags (D2, D3) and the time lags (D3, D4) due to the measuring method, $Tt_2$, $\tau_2$, $Tt_3$ and $\tau_3$. This effective breathing gas oxygen concentration, which has brought about the effective, currently measured oxygen saturation, is called the saturation-effective oxygen concentration in the sense of the present invention. The saturation-effective oxygen concentration is sent as a feedback additively to a first summation point at the output of the controller at the input of the controlled system. The feedback of the saturation-effective oxygen concentration at the patient may be fed back unweighted or weighted. Weighting may be either amplifying or attenuating. This type of feedback of the saturation-effective oxygen saturation represents in this form a controlled variable mixing at the controller output at the beginning of the controlled system, which mixing is predicted by modeling from the time lag (D1) due to the device, physiological time lags (D2, D3) and time lags (D3, D4) due to the measuring method.

A difference value is calculated in the sixth step from the current measured value of the oxygen saturation and the set point of the oxygen saturation and is sent as a control deviation to the input of the controller.

In the seventh step of the process, the controller generates a difference of a breathing gas oxygen concentration at the controller output corresponding to its control characteristic.

The controller output signal is summarily combined with the fed-back saturation-effective oxygen concentration in one result in the eighth step of the process. A manipulated variable for metering, which is sent to the gas-metering unit of the respirator, is determined from the result. The gas-metering unit then controls the metering valves responsible for the oxygen concentration.

The process of controlling the metering of oxygen in a respirator then jumps back into the first step of the process and continuously repeats eight steps one through eight in the course of respiration.

In an especially preferred embodiment of the process, the physiological time response D2, D3 and the time response D4, D5 due to the measuring method are described in the fourth step as a common time lag and imaged by the parameters $Tt_{23}$, $\tau_{23}$.

In another preferred embodiment of the process the first, second and fourth steps of the process are carried out combined and the time response D1 due to the device, the physiological time response D2, D3 and the time response D4, D5 due to the measuring method are combined and imaged in the model as a common time lag, described by the parameters $Tt_{123}$, $\tau_{123}$, and sent in the fifth step of the process additively as a feedback as a saturation-effective oxygen saturation to a first summation point at the output of the controller at the input of the controlled system. In an acceptable approximation, it is not only common but in many cases also advantageous and practical for designing the controller parameters in the technical area of control engineering to replace dead times present in the system, which are unavoidable, e.g., when taking into account measured values that are discrete in time in the measuring component of a control loop, with first-order time function elements (PT-1). The present invention also covers the case in which the dead time component can be transmitted in the modeling into a PT-1 time response or vice versa, the PT-1 time response can also be transmitted into a dead time component, depending on whether the dead time component or PT-1 component is decisive for the expression of the time lag elements.

In a preferred embodiment, the input variables of the breathing gas oxygen concentration at the Y-piece and of the oxygen saturation are replaced in the fifth step of the process, together with the physiological time response and the time response due to the measuring method, namely, D2, D3, D4, D5, with a preset value. In an expanded variant of this preferred embodiment, the preset value is determined from the patient's overall constitution. The constitution parameters of the patient comprise the height, body weight, gestational age, and pathological symptoms. The so-called Apgar score may be used for newborn children as another indicator of this expanded variant; this is a rating score that was developed by the anesthesiologist Virginia Apgar and introduced in obstetrics in 1952, in which pulse rate, breathing, muscle tone, reflexes and skin color of the body are evaluated.

In a preferred embodiment, available measured values, such as oxygen concentration at the Y-piece, flow rate at the Y-piece, respiration rate, tidal volume, heart rate, and setting of the respirator, such as the I:E ratio, form of respiration, respiration pressure, and PV loop are used to determine the physiological and pathological time lags D2, D3 in the fourth step of the process. The heart rate is also determined by the pulse oximeter in another preferred embodiment of this preferred embodiment and is also taken into account in determining the physiological and pathological time lags D2, D3.

An index, which indicates the quality of the measured values and is also contained in the set of measured values of the pulse oximeter besides the measured value of the oxygen saturation and a measured value for the heart rate, is used in a special variant of the process. The index is used, on the one hand, to take into account the current measured $SPO_2$ values in the determination of physiological and pathological time lags D2, D3 in the fifth step of the process in those cases only in which the $SPO_2$ measurement yields reliable values and modeling is not distorted by measuring errors, e.g., due to insufficient contact of the sensor with the hand, foot or ear of the patient. On the other hand, the index is used to prevent measuring errors and artifacts from entering the oxygen saturation control loop unfiltered, i.e., to ensure that only reliable $SPO_2$ values will be used to form the control deviation in the sixth step of the process.

In another preferred embodiment of the process, the humidifying unit transmits, in another, additional step, the current state concerning the filling level of liquid to the control and regulating unit of the respirator.

The control and regulating unit of the respirator determines from this the current volume V2 of the humidifying unit and corrects on this basis the first dead time $Tt_1$ and the first time constant $\tau_1$.

In an expanded embodiment of the process, the time response D1 dependent on the device and the pneumatic run time of a change in the oxygen concentration from the metering means in the respirator to the Y-piece are complemented by a measured value of the current oxygen concentration determined near the patient and/or the curve of the measured value obtained at the Y-piece near the patient. This addition is used to check the modeling of the time response D1 that depends on the device. The measured value of the current oxygen concentration can be obtained here by means of sensors according to an electrochemical or paramagnetic principle of measurement or with a measuring method based on the so-called luminescence quenching or fluorescence quenching. A suitable electrochemical oxygen sensor is described in U.S. Pat. No. 5,827,415, a paramagnetic oxygen sensor is shown in U.S. Pat. No. 4,988,946, and an oxygen sensor that determines the oxygen concentration according to the principle of luminescence quenching is described in U.S. Pat. No. 6,632,402 B2.

No continuous determination of the time response dependent on the device is performed in another embodiment of the process, and the process jumps back into the second step of the process after the device-dependent time response has been determined in the eighth step for the first time and steps two through eight are then repeated in a continuous sequence.

In another embodiment, information concerning the pathological constitution and/or clinical pictures of the patient are also including in the modeling to determine the physiological and pathological time lags D2, D3.

For example, the physiological time lags D2, D3 are prolonged into a time span of 2-5 minutes for the clinical picture PPHN (persistent pulmonary hypertension of newborn) compared to the time lags usually occurring in newborn children in the range of 2 sec to 10 sec.

In another preferred embodiment, the time lag response of the model is checked by a comparison of the time curve of the set value of the oxygen concentration and of the measured $SPO_2$ value. The time curves are compared with one another here on the basis of the locations of rising flanks, sloping flanks, maxima, minima and zero passages and a time difference or phase shift is determined. Adaptation of the model is subsequently performed with the measure of the phase shift, by the parameters ($Tt_1, \tau_1, Tt_2, \tau_2, Tt_3, \tau_3. Tt_3, \tau_2$ and $Tt_{23}, \tau_{23}$ or $Tt_{123}, \tau_{123}$) of the time lag elements being iteratively adapted until the phase shift is compensated. This procedure adapts the model during the operation to the controlled system actually present with the component elements respirator, patient and measuring arrangement for $SPO_2$ measurement.

In an expanded variant of this preferred embodiment, a comparison is performed between the functions of the set value of the oxygen concentration and of the measured $SPO_2$ value in the frequency range to check the modeling and the parameters imaged in the model ($Tt_1, \tau_1, Tt_2, \tau_2, Tt_3, \tau_3, Tt_3, \tau_2$ and $Tt_{23}, \tau_{23}$ or $Tt_{123}, \tau_{123}$) of the time lag elements besides the comparison of the time curve of the set value of the oxygen concentration and of the measured $SPO_2$ value. One possibility of comparing the functions of the set value of the oxygen concentration and of the measured $SPO_2$ value in the frequency range is to form the transfer function with the set value of the oxygen concentration as an input signal and with the measured value of the oxygen saturation as the output signal. Time intervals of the two time curves, which intervals are equidistant in time, are determined now; they are synchronized by means of the phase shift determined in the form of period durations and transformed into the frequency range. The transformation is preferably performed over a plurality of period durations to suppress random measurement results. The use of a plurality of period durations makes it, furthermore, possible to ignore the phase synchronization of the time intervals as soon as the plurality of period durations is large enough compared to the phase shift determined in the time curve of the two signals being considered. Considering more than 30 to 100 period durations is a practical value, so that phase shifts in the range of 5° to 30° can be ignored in terms of their effect on the result of the transformation. One possibility of triggering the transformation in terms of time is to use the heart rate, which is also made available by the pulse oximeter in the set of measured values provided by the $SPO_2$ measurement.

The transformation from the time span F(t) into the frequency range, or even into the so-called image range F(p), may be performed according to usual mathematical methods, e.g., by means of the Laplace transform, the z transform or the discrete Fourier transform (DFT) or the Fast Fourier Transform (FFT) method.

To suppress interference effects and to limit the frequency range, filtration of the measured data, which is common according to the state of the art, is performed prior to the performance of the transformation by means of a low-pass filter, whose cut-off frequency is preferably selected to be in a range of 5-10 Hz.

Setting parameters of the respirator, measured values of an ECG monitor and measured values of the $SPO_2$ monitor, as well as the curve of the measured values are also included in another preferred embodiment of the present invention to determine the time lags due to the device and the time lags due to the patient. The setting parameters of the respirator are information on the tube system, such as length, type and diameter, on resistance and compliance of the device-to-patient tube connection, information on connected accessories such as humidifying unit with data on volume, filling level and pneumatic resistance, as well as data on dead space and pneumatic resistance of sensors located near the patient for the flow rate and carbon dioxide, as well as measured values of such sensors, such as flow rate and $CO_2$ concentration.

In an expanded variant of this other preferred embodiment, the control characteristic (P, I, D) is adapted and changed in the seventh step of the process on the basis of a patient classification according to constitution, age and certain clinical pictures, for example, PPHN (persistent pulmonary hypertension of newborn). A classification of the constitution of newborn children may be performed, for example, according to the so-called Apgar score. This rating score, developed by the anesthesiologist Virginia Apgar, takes into account pulse, breathing, muscle tone, reflexes and the skin color of the body.

In an alternative embodiment of the process according to the present invention, the time lags and their determinations are integrated in a common routine, wherein at least one time response of a respirator, a time response of a measuring arrangement for measuring the oxygen saturation or a time response of a patient are simulated in at least one time function element, a saturation-effective oxygen concentration is determined from a set value of the oxygen concentration in the respirator and a curve of the set value of the oxygen concentration and the at least one time function element, a measured value of a current oxygen saturation is determined, a difference value of the oxygen concentration is determined from a set point of the oxygen saturation and the measured value of the current oxygen saturation, and the difference value of the oxygen concentration with the saturation-effective oxygen concentration is linked to a set value of the oxygen concentration and the set value of the oxygen concentration in the respirator is used to set the metering of the oxygen concentration.

The device for obtaining a uniform blood gas oxygen concentration is used especially in a neonatal intensive care unit (NICU). The process and device for obtaining a uniform blood gas oxygen concentration is used in this application to reliably prevent oxygen levels above a saturation value of 95% from occurring even for a short time. Damage to the eyes, resulting in partial or total blindness (retinopathy of premature: ROP) may potentially [develop—verb missing in original—Tr.Ed.] especially in immature premature babies already beginning from a blood oxygen saturation above 93%. Damage to the eyes can be avoided by means of the process and device for obtaining a uniform blood gas oxygen concentration.

Besides use in a neonatal intensive care unit (NICU), the device for obtaining a uniform blood gas oxygen concentration may be used in an intensive care unit (ICU) for adult patients. Long-term respiration of patients with excessively high oxygen concentrations may lead to damage to the lungs (development of atelectases, pulmonary vasodilation). To avoid insufficient oxygen supply (hypoxia), a high oxygen saturation close to 100% in the blood is usually preset in clinical practice and the gas is metered for this reason with high oxygen concentration values. The high preset value of the oxygen saturation in the blood is replaced by the process according to the present invention by the control loop, so that target values of an oxygen saturation of 97% in the blood can also be set without hypoxia being able to develop, because this is prevented by the use of the control. Especially in patients with reduced pulmonary ventilation and chronically increased arterial carbon dioxide concentrations, an unadapted metering of oxygen in the breathing gas leads to a reduction of the respiratory drive and an increase in the carbon dioxide concentration values in the blood. The control of respiration with the use of the process according to the present invention for obtaining a uniform blood gas oxygen concentration and of the device according to the present invention for obtaining a uniform blood gas oxygen concentration can avoid oxygen overdosage especially in these cases because feedback of the $SPO_2$ value into the respiration control, which feedback is adapted to the patient and to the conditions of the device and of the measuring method, is reduced, in principle, the range of variation of the oxygen concentration and overdosage and underdosage effects of the control loop are avoided.

A special possibility of using the device for obtaining a uniform blood gas oxygen concentration is given in situations in which the medical care of very many patients is greatly compromised by a clinical care situation compared to the usual one. This happens especially when very many patients must be cared for by a comparatively small number of skilled medical staff. Such situations occur, for example, as an effect of natural disasters or accidents involving a large number of injured or under the effect of the spread of viral diseases or epidemics over large areas.

The process and device for obtaining a uniform blood gas oxygen concentration help the skilled medical clinical staff or the staff of the mobile emergency care to guarantee reliable respiration of the patients due to the uniform blood gas oxygen concentration without having to manually check and modify the therapy of the individual patients in the further course of respiration after presetting starting parameters of the respiration for the individual patient. This offers the possibility of respirating a large number of patients with a small number of skilled medical staff and of prioritizing the personal and manual therapy to the patients with the most severe clinical pictures and acute, life-threatening situations.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
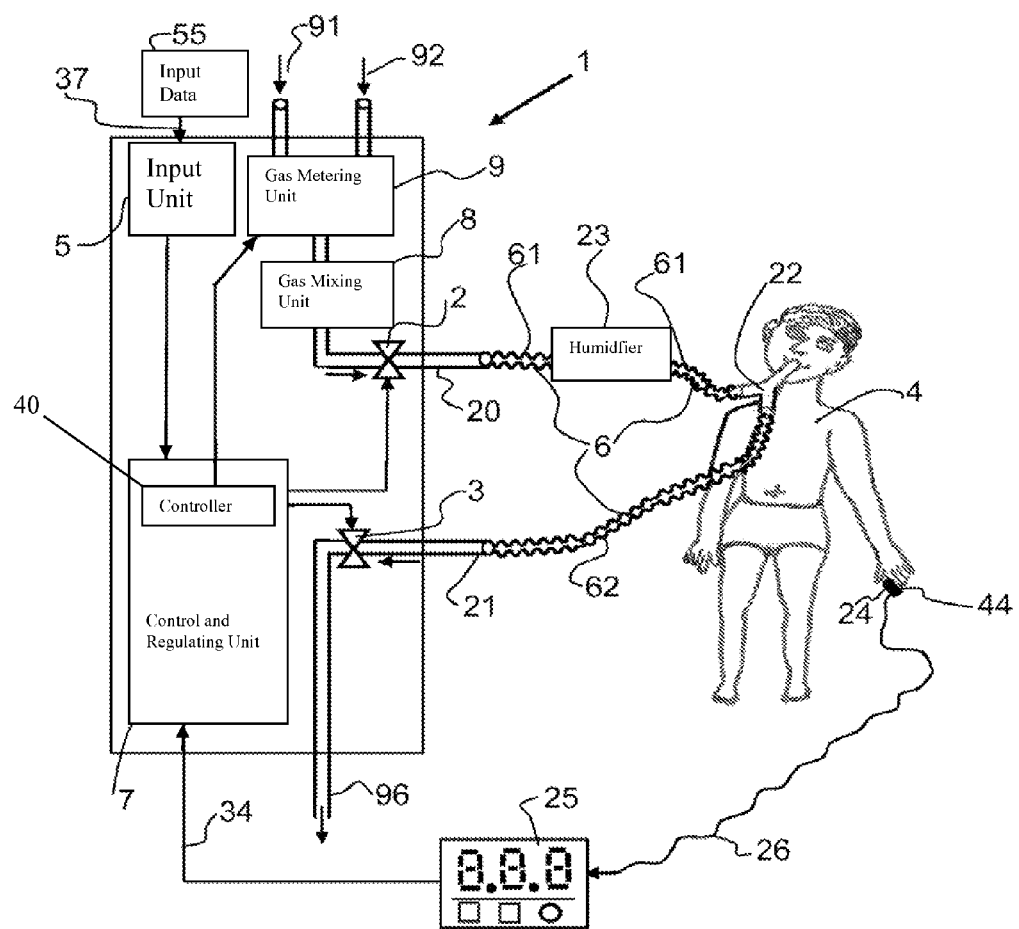
FIG. 1 is a schematic view of a respirator, tube system, patient and oxygen saturation measuring means.

Referring to the drawings in particular, FIG. 1 shows a schematic view of the respirator, tube system, patient and oxygen saturation-measuring means. An inspiration valve 2, an expiration valve 3, an input unit 5, a control and regulating unit 7, a gas-mixing unit 8 designed as a tank and a gas-metering unit 9 are present as essential elements of respirator 1. A first gas supply port 91 and a second gas supply port 92 are provided for supplying oxygen and air into the gas-metering unit 9 of respirator 1. Gas is sent to a patient 4 from the respirator 1 during inspiration via a gas path 4 and a first gas port 20 and a Y-piece 22 and gas is sent to a patient 4 from the respirator 1 during expiration via a second gas port 21. The expired gas escapes via the gas outlet 96 into the environment. Gas path 6 is preferably designed as a breathing tube system with an inspiration tube 61 and with an expiration tube 62. A humidifying unit 23 is arranged in the gas path of the inspiration tube 61 to patient 4. A sensor 24 for measuring the oxygen saturation is arranged at the finger 44 of patient 4. Sensor 24 is electrically connected to an oxygen saturation-measuring unit 25 via a sensor line 26.

The oxygen saturation-measuring unit 25 is connected to the control and regulating unit 7 of respirator 1. The measured $SPO_2$ value 34 is made available via this connection to a controller 40 for regulating the oxygen concentration within the control and regulating unit 7 of respirator 1. An input data set 55 with a set point 37 of the oxygen saturation is transmitted via the input unit 5 to the controller 40 within the control and regulating unit 7. A control deviation, which is sent to the input of the controller, is determined from the set point 37 of the oxygen saturation and the measured $SPO_2$ value. Controller 40 responds according to the control characteristic, for example, according to a proportionally-integrally-differentially acting controller design. Controller 40 is preferably designed as a digital controller as a part of the control and regulating unit 7. The digital controller 40 can be described by mathematical relationships or sets of equations and imaged in the digital control procedure or the control characteristic may be imaged in the form of look-up tables. The look-up table converts a set of input data, comprising a set point of the oxygen saturation ($SPO_{2\_Soll}$) 37 and a measured value of the oxygen saturation ($SPO_{2\_Ist}$) 34, numerically into a difference value of a breathing gas oxygen concentration ($\Delta FiO_2$) as an output signal of controller 40. The output signal of controller 40 acts on the gas-metering unit 9, in which the concentration of oxygen present in the breathing gas is set.

Figure 2:
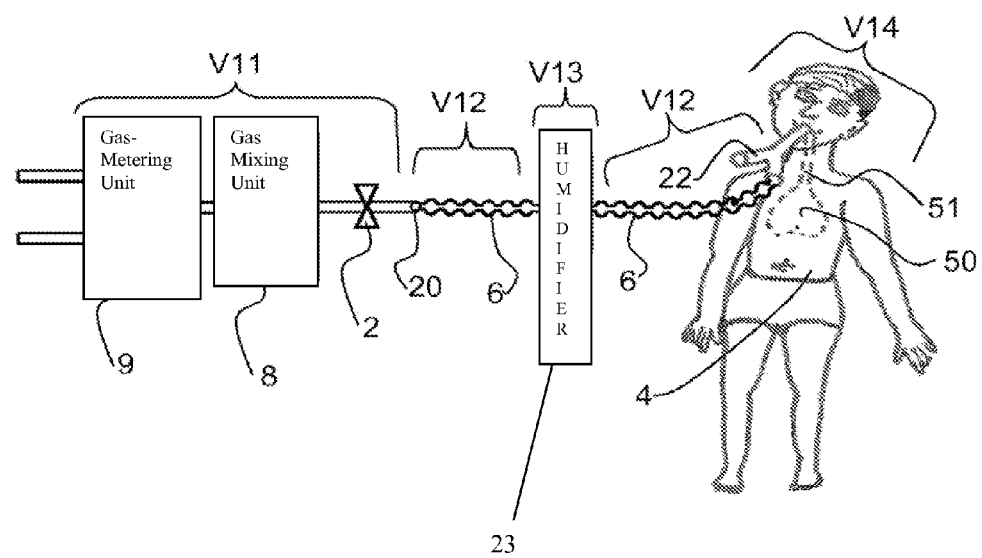
FIG. 2 is a schematic view of the pneumatic connection of the volumes comprising the tube system, humidifying unit and patient.

FIG. 2 shows a view of the pneumatic connection of the volumes in the inspiratory gas path of the patient. The gas-metering unit 9, gas-mixing unit 8, inspiration valve 2 and inspiratory gas outlet 20 together form a first volume V11. The first volume V11 is typically on an order of magnitude of about 1,000 mL. The inspiration tube 61 and Y-piece 22 together form a second volume V12. The second volume V12 is typically on an order of magnitude of 100 mL, depending on the length of the tube. The humidifying unit 23 represents a third volume V13. The third volume V13 is typically on an average order of magnitude of 250 mL. Depending on the filling level of water in the humidifying unit 23, a range of 100 mL to 500 mL is obtained for the third volume 13.

A fourth volume V14 is formed from the lungs 50 of patient 4 and the bronchial area 51 of patient 4. The fourth volume V14 is typically on an order of magnitude of 1 mL for very immature newborn babies, in the range of 5 mL for newborn babies (neonates), in the range of 300 mL for children and in the range of 500 mL for adults.

Figure 3:
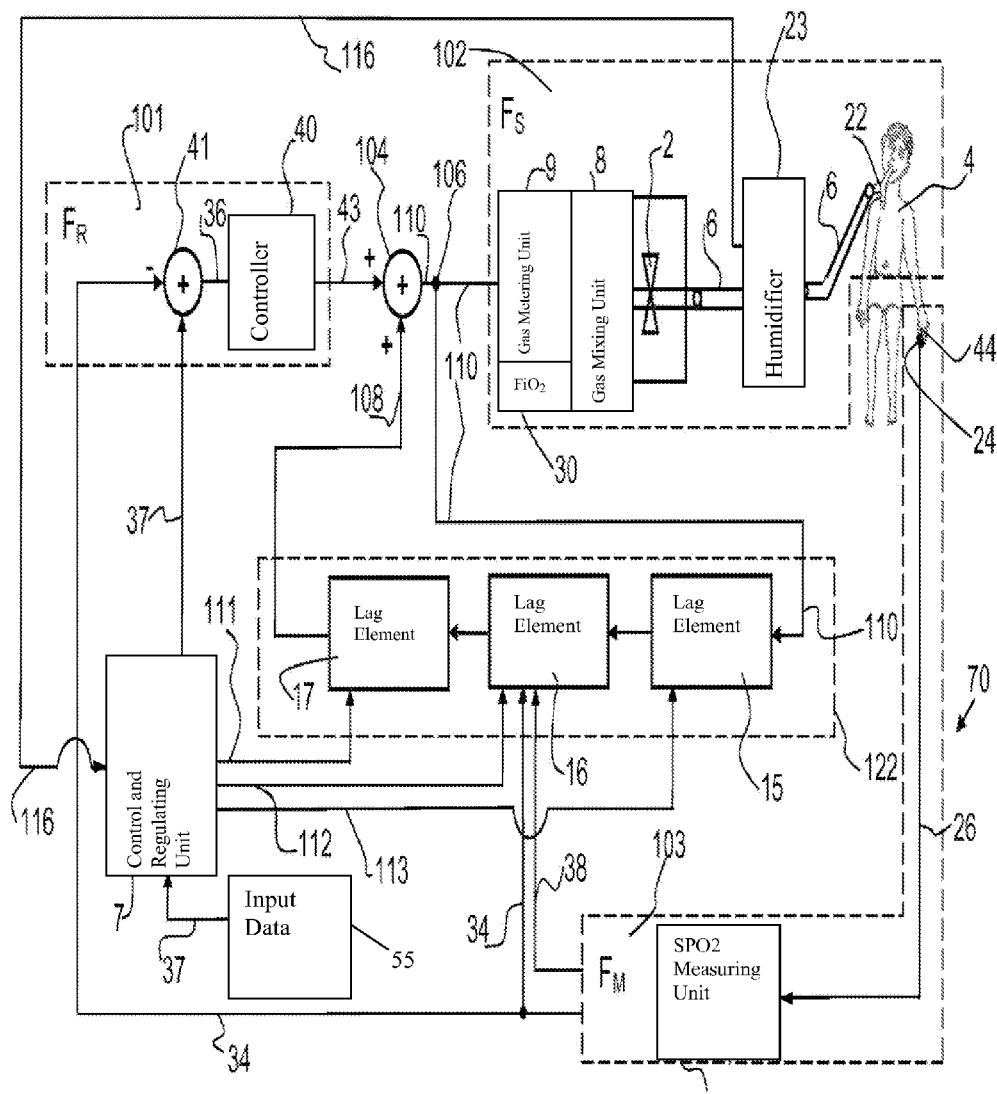
FIG. 3 is a first schematic view of a closed control loop.
Figure 3A:
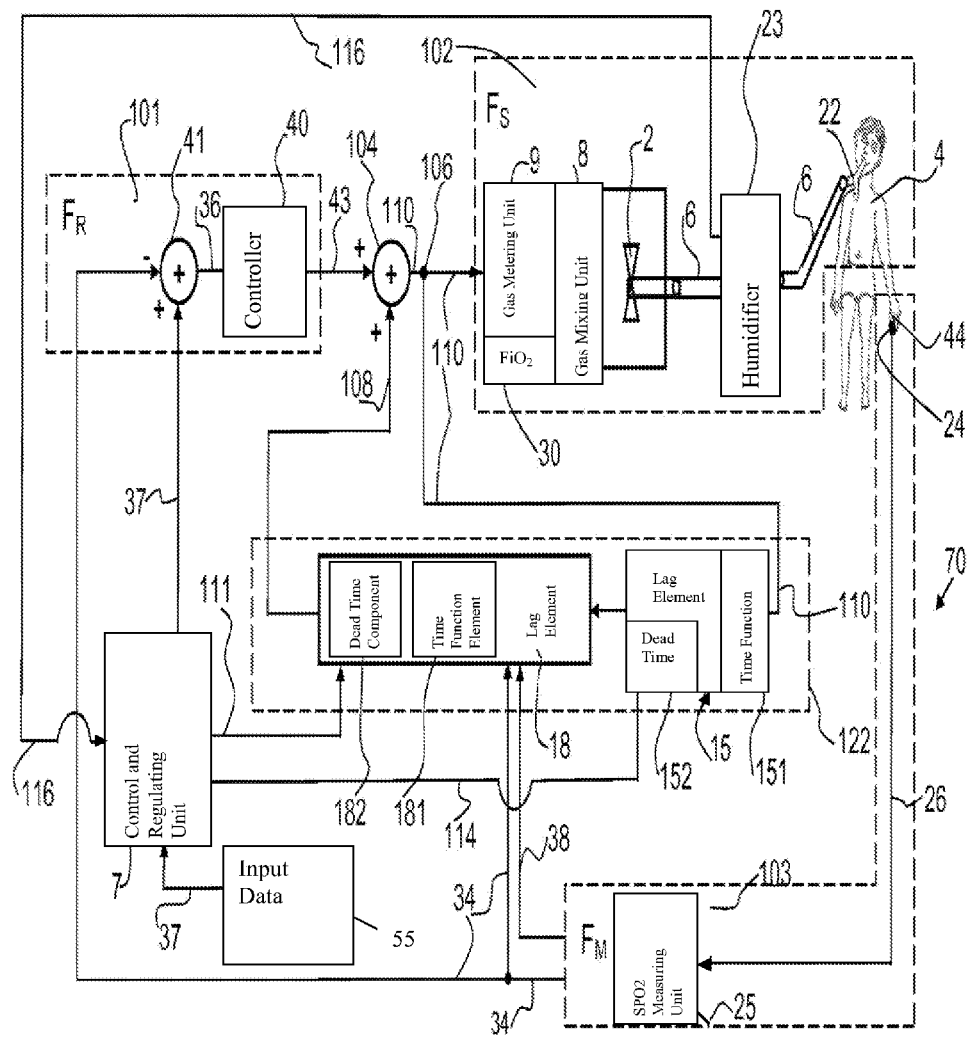
FIG. 3a is a second schematic view of a closed control loop.
Figure 3B:
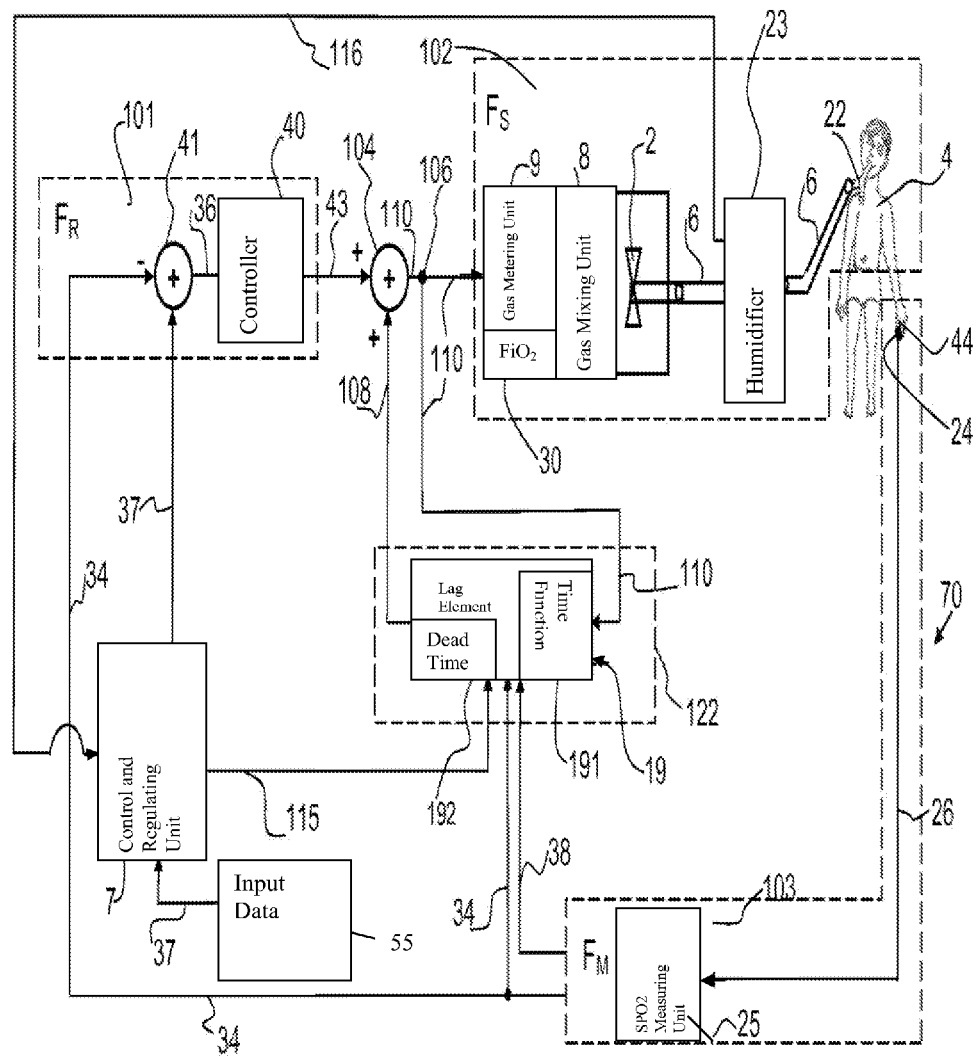
FIG. 3b is a third schematic view of a closed control loop.

FIG. 3 and FIGS. 3a and 3b show views of the closed control loop with oxygen saturation-measuring means, patient, pneumatic patient connection to the respirator and time function elements formed by models. Identical components are designated by the same reference numbers as in FIG. 1 and FIG. 2. The closed control loop 70 comprises a controller element 101, a controlled system 102, a time modeling component 122 and a measuring component 103. Furthermore, a first summation point 104 and a first branching point 106 are arranged in series with controller 40. The control loop 70 is preferably designed as a part of the control and regulating unit 7 (FIG. 1), and controller 40 is designed in the digital form in another preferred manner.

An input data set 55 transmitted by the input unit 5 (FIG. 1) with a set point of the oxygen saturation 37 is sent as a command variable to the controller 40 via the control and regulating unit 7. Device parameters of the respirator 1 (FIG. 1), of the gas path 6 and of the humidifier 23 are made available by the control and regulating unit 7 by means of a first data connection 111 and also included for modeling time lag elements 15. Furthermore, patient parameters are made available by the control and regulating unit 7 by means of a second data connection 112 and also included for modeling time lag elements 16. In addition, measured parameters of the measuring arrangement comprising the $SPO_2$ sensor 24 and $SPO_2$ monitor 25 are made available by the control and regulating unit 7 by means of a third data connection 113 and also included for modeling time lag elements 17. The humidifying unit is in connection with the control unit 7 via a sixth data connection 116. A state of the liquid feed to the humidifying unit 23 or of a filling level of the liquid reservoir of the humidifying unit 23 can be transmitted to the control unit 7 via the fourth data line. Control unit 7 can thereupon correspondingly adjust the device parameters and make them available to the modeling component 122 by means of the first data connection 111.

The controlled system 102 comprises a patient 4, the humidifying unit 23, a gas-metering unit 9, a gas-mixing unit 8, an inspiration valve 2, a breathing tube system as a gas path 6 and a Y-piece 22 for connecting the breathing tube system 6 to the patient 4.

The measuring component 103 comprises an $SPO_2$ sensor 24 at the finger 44 of patient 4 with a sensor line 26 to an $SPO_2$ monitor 25. The output signal of the $SPO_2$ monitor 25 is sent as a controlled variable as a set of measured values of the oxygen saturation 34 to the controller input 41 of controller 40 in the controller element 101. Controller element 101 comprises a controller 40, a controller input 41, which is designed to form the difference from the set point and actual value, and the controller output 43, at which the response of the controller 40 is present corresponding to the control characteristic.

The set point of the oxygen saturation 37 is available at the controller input 41 as a command variable and the measured value of the oxygen saturation 34 is present as a controlled variable at the actual value input. The set point 37 of the oxygen saturation $SPO_2$ is typically in a range of 87% to 97%. A difference value of the oxygen saturation 36 is formed in the controller input 41 from the set point 37 of the oxygen saturation and the measured $SPO_2$ value data set 34 and is made available to the controller 40. The measured value 34 of the oxygen saturation $SPO_2$ is typically in a range of 85% to 100%.

The difference value 36 of the oxygen saturation $SPO_2$ is typically in a range of ±5%. Controller 40 responds with a response signal at its controller output 43 according to the control characteristic, for example, according to a proportionally-integrally-differentially acting control design.

Modeling component 122 comprises time lag elements with device-dependent time lags 15, with patient-dependent time lags 16 and with time lags 17 due to the measuring method.

The modeling component 122 images the relationship in time between a change in the oxygen concentration starting from the metering means 9 to the Y-piece 22 at patient 4 in the first time lag element 15. The run time lag of the change in oxygen concentration imaged in the first time lag element 15 is typically in the range of 3 sec to 20 sec.

The volumes V1 (respirator) 11 (FIG. 2), V2 (breathing tube system) 12 (FIG. 2), V3 (humidifying unit) 13 (FIG. 2) are assigned in this modeling hypothesis to the first time lag element 15, and volume V4 (bronchial area of the patient) 14 (FIG. 2) is assigned to the second time lag element 16.

The modeling component sends a feedback signal 108 to the first summation point 104 located in the input of the controlled system 102. The assignment of the volumes 15, 16, 17 and the division into dead times 152 (FIG. 4), 162 (FIG. 5), 172 (FIG. 6) and first-order time function elements 151 (FIG. 4), 161 (FIG. 5), 171 (FIG. 6), which was performed in the time lag elements 15, 16, 17, are performed in this selected modeling hypothesis such that the controller design, the calculation performance and the components of the respirator 1 (FIG. 1) are taken into account. A combination of control loop components and also a conversion of control loop components into the adequate other assignments and compositions are common in the practice of control engineering, such as, for example, the conversion of parallel control loop structures into serial control loop structures and vice versa, or the selection of a different design with subordinate control loops, as well as the approximation of dead time function elements with first-order time function elements.

The second time lag element 16 and the third time lag element 17 cannot be determined separately in the practical implementation without an expanded measuring effort and are combined into a common, fourth time lag element 18, comprising a common, fourth dead time component 182 and a common, fourth first-order time function element (PT-1) 181. Such an arrangement with a first time lag element 15 and with a common, fourth time lag element 18 is shown in FIG. 3a. The second and third data lines 112, 113 are combined in a fourth data line 114 in this embodiment according to FIG. 3a. Identical components are designated by the same reference numbers as in FIGS. 1, 2 and 3. The second time lag element 16 and the third time lag element 17 together lead to a typical time lag 18 ranging from a few seconds to a time of 3 minutes to 6 minutes.

Another practical simplification of the modeling element 122 can be performed by a combination of the first time lag element 15 with the second time lag element 16 and the third time lag element 17 in a common, fifth time lag element 19. Such an arrangement with a summary, common, fifth time lag element 19 is shown in FIG. 3b.

The common, fifth time lag element 19 may be represented by a common, fifth dead time component 192 and a common, fifth first-order time function element (PT-1) 191. The present invention also covers the case in which the dead time component can be transmitted into a PT-1 time response or, conversely, the PT-1 time response can be transmitted in the modeling into a dead time component, depending on whether the dead time component or PT-1 component is decisive for the expression of the time lag elements 15, 16, 17, 18, 19.

Identical components are designated by the same reference numbers as in FIGS. 1, 2 and 3. The first, second and third data lines 111, 112, 113 are combined in a fifth data line 115 in this embodiment according to FIG. 3b. The typical common time lag 19 as a combination of the three time lags 15, 16, 17 is in the range from half a minute to 7 minutes.

Modeling element 122 cooperates in the control loop 70 with the controlled system 102, measuring component 103 and controller element 101 in the following manner: The controller output signal 43 and the feedback signal 108 of the modeling means 122 are sent to the first summation point 104. The feedback signal 108 of modeling means 122 is likewise sent to the first summation point 104.

A first branching point 106, from which the summation signal 110 is sent to the gas-metering unit 9, on the one hand, and additionally to the modeling element 122 as an input variable, is arranged in series with the first summation point 104. The set value of the oxygen concentration 30 is corrected in the gas-metering unit 9 on the basis of the summation signal 110. The output signal of the SPO$_2$ monitor 25 with the set of measured oxygen saturation values 34 including the heart rate 38 is sent to the second time function element 16 within the modeling component 122. The measured oxygen saturation value 34 and the measured value of the heart rate 38 are provided in the practical embodiment with an index, which indicates the quality of the measurement. The variables 108, 110 may be sent to the corresponding elements weighted or unweighted; the variables 108, 110 are shown as unweighted variables in this exemplary embodiment according to FIG. 3. For implementation in practice, the weighting may be preferably performed such that the quality index is included.

Figure 4:
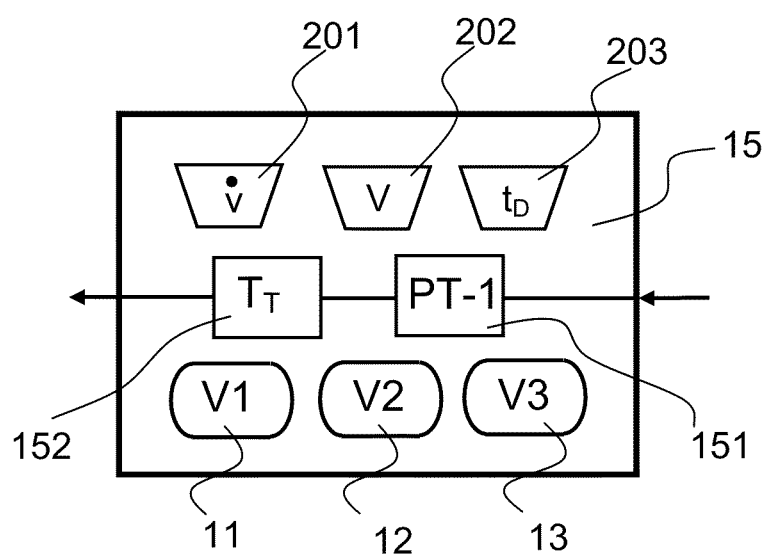
FIG. 4 is a view of modeling for the time response dependent on the device.

FIG. 4 shows the composition of the device-dependent time lags in detail. Identical components are designated by the same reference numbers as in FIGS. 3, 3a and 3b.

The volumes V1 (respirator) 11, V2 (breathing tube system) 12, V3 (humidifying unit) 13, which cause the time lag and which are transmitted by the control and regulating unit (FIG. 3), and the changes in these respective volumes during respiration, e.g., due to a lowering of the filling level in the liquid reservoir of the humidifying unit 23, as well as the other device parameters transmitted by the control and regulating unit (FIG. 3), for example, the flow values 201, volume-metering values 202, and actuation time lag 203 of the gas-metering means, are taken into account in the modeling of the first time lag element 15. The first time lag element 15 is split into a first first-order time function element 151 and a first dead time 152.

Figure 5:
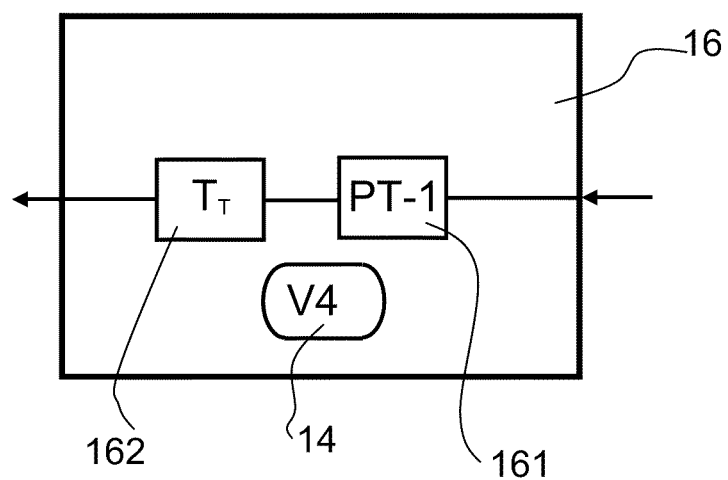
FIG. 5 is a view of modeling for the patient-dependent time response.

FIG. 5 shows the composition of the patient-dependent time lags in detail. Identical components are designated by the same reference numbers as in FIGS. 3, 3a and 3b.

Volume V4 (bronchial area of the patient) 14, which is transmitted by the control and regulating unit (FIG. 3), as well as the patient parameters transmitted by the control and regulating unit (FIG. 3) are taken into account in the modeling of the second time lag element 16. The second time lag element 16 is split into a second first-order time function element 161 and a second dead time 162.

Figure 6:
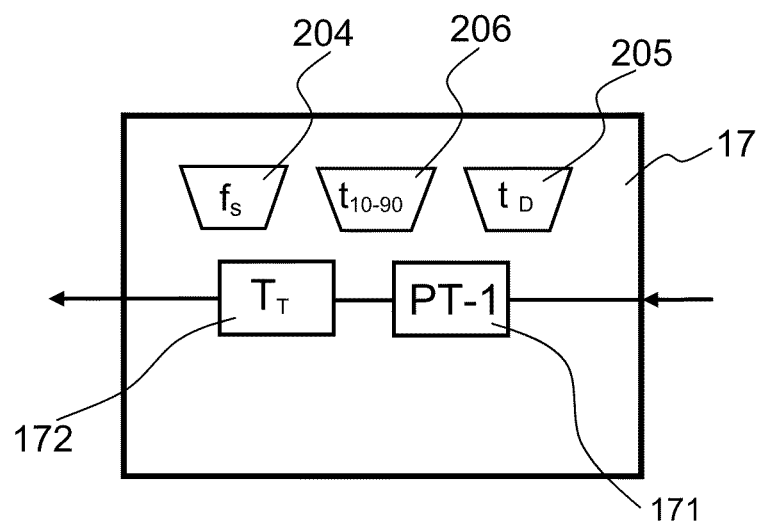
FIG. 6 is a view of modeling for the time response due to the measuring method.

FIG. 6 shows the composition of the time lags due to the measuring method in detail. Identical components are designated by the same reference numbers as in FIGS. 3, 3a and 3b.

The measuring component 103 is taken into account in the modeling of the third time lag element 17. The third time lag element 17 is composed of the measuring characteristic of the oxygen saturation sensor 24, the data logging and measured value processing of the oxygen saturation-measuring unit 25 and the data transmission from the oxygen saturation-measuring unit 25 to the control and regulating unit 7 of respirator 1 (FIG. 1). The measuring properties of the SPO$_2$ sensor 24, for example, a response time 206, and the measuring properties of the SPO$_2$ monitor 25, for example, a sampling rate 204 and a processing time lag 205 due to the data transmission from the SPO$_2$ monitor 25 to the respirator 1 (FIG. 1) and signal processing in the SPO$_2$ monitor 25 and in the control and regulating unit 7 are taken into account in the modeling of the third time lag element 17.

The third time lag element 17 is split into a third first-order time function element 171 and a third dead time 172.

Figure 7:
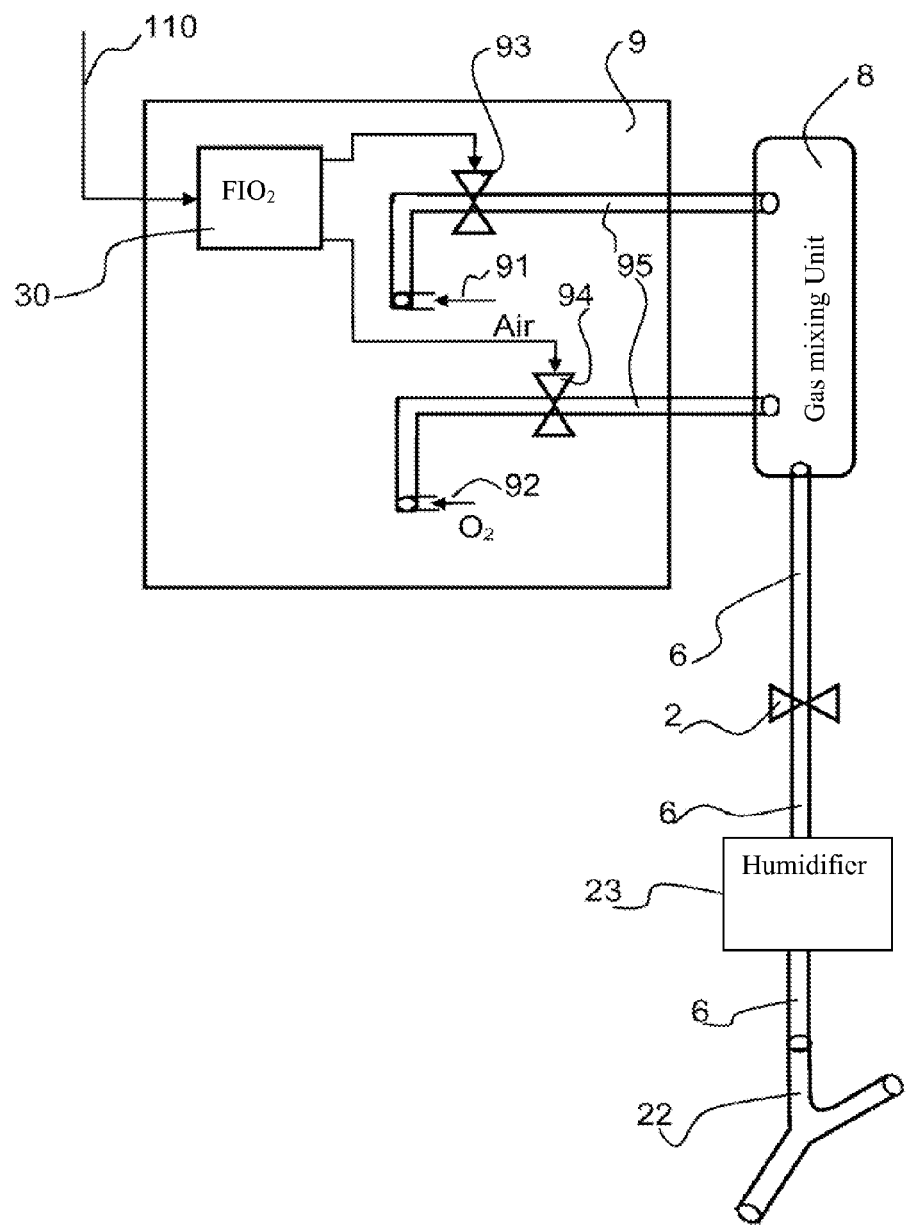
FIG. 7 is a detailed view of gas metering.

FIG. 7 shows a view of the gas-metering means in detail. The gas-metering unit 9 comprises a first metering valve 93 and a second metering valve 94, a first gas supply port 91 and a second gas supply port 92 for supplying oxygen and air into the gas-metering unit 9, a gas-mixing unit 8 designed as a tank-type storage unit, as well as internal gas connection lines 95.

Furthermore, an inspiration valve 2 for controlling the respiration and a breathing tube system 6, as well as a Y-piece 22 for connecting the respirator (FIG. 1) to the patient 4 (Figure) are shown. Pressurized oxygen and air reach the metering valves 93, 94 via the gas supply ports 91, 92. The summation signal 110, which is sent from the summation point 104 (FIGS. 3, 3a, 3b) to the gas-metering unit 9, corrects the set value of the oxygen concentration 30. Based on this set value of the oxygen concentration 30, the gas-metering unit 9 controls the metering valves 93, 94 and thus generates an oxygen-air mixture with the preset oxygen concentration. The oxygen-air mixture is kept ready in the gas-mixing unit 8 for metering the oxygen-air mixture via the inspiration valve.

Figure 8:
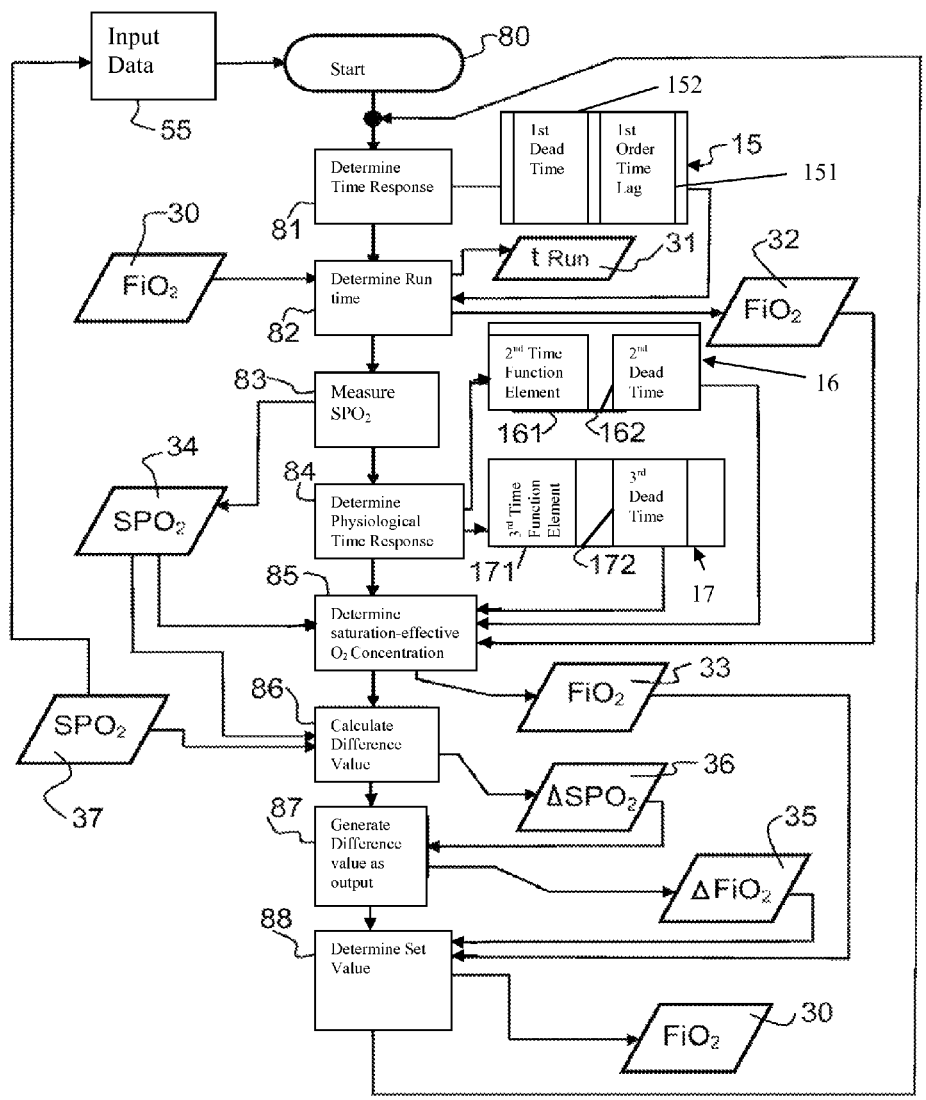
FIG. 8 is a schematic view of a sequence of steps for carrying out the process according to the present invention.

FIG. 8 schematically shows a sequence of steps for carrying out the process according to the present invention.

The process begins with a start 80, wherein an input data set 55 with a set point of an oxygen saturation concentration 37 is read.

A device-dependent time response is determined in a first step 81 from a first time lag element 15 as a series connection with a first first-order time lag element 151 and with a first dead time 152.

A run time $t_{RUN}$ 31 of a change in the oxygen concentration through the feed lines 6 (FIG. 1) and the humidifying unit 23 (FIG. 1) up to the Y-piece 22 (FIG. 1) is determined by the metering means in the respirator 9 (FIG. 1) from a set value of the oxygen concentration 30, the first first-order time function element 151 and the first dead time 152 in a second step 82, and an oxygen concentration $FiO_2$ 32 at the Y-piece 22 (FIG. 1) is calculated by means of the run time $T_{RUN}$ 31. The oxygen concentration $FiO_2$ fed to the patient at the Y-piece is typically in a range from 21 vol. % to 100 vol. %.

An oxygen saturation measurement is performed in a third step 83 by the $SPO_2$ monitor 25 (FIG. 1) by means of an $SPO_2$ sensor 24 (FIG. 1) connected to it and a set of measured oxygen saturation values $SPO_2$ 34 is determined.

A physiological time response, which is due to the oxygen transport from the air in the lungs into the blood circulation, and a time response of the $SPO_2$ sensor 24 (FIG. 1), which depends on the measuring method, is determined in a fourth step 84 combined with the data transmission from the $SPO_2$ monitor 25 (FIG. 1) to the respirator 1 (FIG. 1) and a signal processing in the control and regulating unit 7 with a second time lag element 16 and with a third time lag element 17 as a series connection comprising a second first-order time function element 161 and a second dead time 162 and a third first-order time lag element 171 and a third dead time 172.

The saturation-effective oxygen concentration $FiO_2$ 33, which has caused the current measured value of the oxygen saturation 34, is determined in a fifth step 85 from the breathing gas oxygen concentration $FiO_2$ 32 at the Y-piece 22 (FIG. 1) and the second time function element 161 and the second dead time 162, as well as the third time function element 171 and the third dead time 172 and the measured oxygen saturation data set 34. The saturation-effective breathing gas oxygen concentration $FiO_2$ 33 determined is typically in a range of 16 vol. % to 100 vol. %. The saturation-effective breathing gas oxygen concentration $FiO_2$ 33 is sent to the input of the controlled system 102 (FIG. 3) in the eighth step.

A difference value 36 is calculated in a sixth step 86 from the current measured value 34 of the oxygen saturation $SPO_2$ and the set point 37 of the oxygen saturation $SPO_2$ and the difference value $\Delta SPO_2$ 36 is formed. The measured value 34 of the oxygen saturation $SPO_2$ is typically in a range from 85% to 99%.

The set point 37 of the oxygen saturation $SPO_2$ is typically in a range from 87% to 97%.

The difference value 36 of the oxygen saturation $SPO_2$ is typically in a range of ±5%.

A difference value $\Delta FiO_2$ 35 of the breathing gas oxygen concentration is generated as an output variable in a seventh step 87 from the difference value $\Delta SPO_2$ 36 of the oxygen saturation as an input variable of the controller 40 according to the control characteristic of controller 40 (FIG. 3). The difference value $\Delta FiO_2$ 35 of the breathing gas oxygen concentration and the oxygen saturation $SPO_2$ is typically in a range of ±5%.

In an eighth step 88, the $\Delta FiO_2$ output variable 35 is additively linked with the saturation-effective breathing gas oxygen concentration $FiO_2$ 33 and a set value 30 of the breathing gas oxygen concentration $FiO_2$ is determined. This set value of the breathing gas oxygen concentration $FiO_2$ 30 is sent to the gas-metering unit 9 (FIG. 1) of respirator 1 (FIG. 1). The gas-metering unit 9 (FIG. 1) of respirator 1 (FIG. 1) updates the metering of the oxygen concentration with the set value of the breathing gas oxygen concentration $FiO_2$ 30. The process subsequently jumps back into the first step 81 and is continued in a continuous sequence.

While specific embodiments of the invention have been described in detail to illustrate the application of the principles of the invention, it will be understood that the invention may be embodied otherwise without departing from such principles.

What is claimed is:

1. A process for controlling a respirator, the respirator comprising a control and calculating unit, a gas path, a gas-mixing unit, a gas-metering unit, a measuring arrangement for measuring an oxygen saturation, an input unit and a controller, the process comprising the steps of:
   providing a humidifying unit;
   providing at least one time function element;
   simulating one or more time responses of the respirator and said humidifying unit, the measuring arrangement for measuring an oxygen saturation and a patient in said at least one time function element;
   providing a set value of an oxygen concentration in the respirator, wherein a run time of a change in the oxygen concentration through at least said humidifying unit is determined based on at least said set value of said oxygen concentration and said one or more time responses of said respirator and said humidifying unit;
   determining a saturation-effective oxygen concentration based on at least said run time of said change in said oxygen concentration;
   determining a measured value of a current oxygen saturation;
   providing a set point of an oxygen saturation to the respirator;
   determining a difference value of an oxygen concentration from said set point of the oxygen saturation and said measured value of the current oxygen saturation; and
   linking said difference value of the oxygen concentration with said saturation-effective oxygen concentration to form an updated set value of the oxygen concentration and setting a metering of said oxygen concentration in the respirator based on said updated set value of the oxygen concentration, wherein said updated set value of the oxygen concentration is provided as input to said at least one time function element.

2. A process in accordance with claim 1, wherein the set value of the oxygen concentration is complemented by a measured value of the oxygen concentration.

3. A process in accordance with claim 1, wherein the time curve of the set value is compared with a time curve of the measured value of the oxygen saturation and the modeling of said one or more time responses is changed based the time curve comparison.

4. A process in accordance with claim 1, wherein a frequency response of the set value of the oxygen concentration is compared with a frequency response of the measured value of the oxygen saturation and modeling of said one or more time responses is changed based on the frequency response comparison.

5. A process in accordance with claim 1, wherein a quality index of the measured oxygen saturation values is sent to the control and calculating unit and the measured value of the oxygen saturation is changed based on the quality index of the set of measured values.

6. A process for controlling a respirator, said respirator comprising a control and calculating unit, a gas path, a gas-mixing unit, a gas-metering unit, a measuring arrangement for measuring an oxygen saturation, an input unit, a controller and a humidifying unit, the process comprising the steps of:
providing at least one time function element;
simulating at least one time response of at least the respirator and the humidifying unit in said at least one time function element;
providing a set value of an oxygen concentration to the respirator;
determining a saturation-effective oxygen concentration based on said set value of the oxygen concentration in the respirator and a curve of the set value and said at least one time function element;
determining a measured value of a current oxygen saturation;
providing a set point of an oxygen saturation to the respirator;
determining a difference value of the oxygen concentration based on said set point of the oxygen saturation and said measured value of said current oxygen saturation;
linking the difference value of the oxygen concentration and the saturation-effective oxygen concentration to a new set value of the oxygen concentration and setting a metering of the oxygen concentration of the respirator based on said new set value of the oxygen concentration;
adjusting said at least one time response of at least the respirator and the humidifying unit based on said new set value of the oxygen concentration.

7. A process for controlling a respirator with an expiration valve, a control and calculating unit, a gas path, a gas-mixing unit, a gas-metering unit with a set value of the oxygen concentration, a measuring arrangement for measuring an oxygen saturation, an input unit, a humidifying unit and a controller, the process comprising the steps of:
a) determining a device-dependent time response of the respirator, said humidifying unit and the gas path in a first step and simulating said device-dependent time response in at least one time lag element, said gas path comprising a feed line connected to said humidifying unit and a Y-piece;
b) determining a run time of a change in the oxygen concentration from a metering means in the respirator through said humidifying unit to said Y-piece based on a set value of the oxygen concentration and a curve of the set value of the oxygen concentration and said at least one time lag element and calculating a patient-side oxygen concentration based on said run time of said change in said oxygen concentration;
c) performing an oxygen saturation measurement in a third step with the measuring arrangement and determining a set of measured oxygen saturation values;
d) determining a first time response and a second time response in a fourth step and simulating said first time response and said second time response in at least one other time lag element, said first time response corresponding to a time response of oxygen being transported from inspired air into a blood circulation, said second time response being dependent on a measuring method, said second time response being based on the measuring arrangement used to measure the oxygen saturation;
e) determining a saturation-effective oxygen concentration in a fifth step from the patient-side oxygen concentration and the at least one lag element and at least one other time lag element;
f) forming a difference value in a sixth step based on the set of measured oxygen saturation values and a set point of the oxygen saturation;
g) generating a breathing gas oxygen concentration via a controller based on the difference value in a seventh step; and
h) linking the breathing gas oxygen concentration in an eighth step with the saturation-effective oxygen concentration to a corrected set value of the oxygen concentration, said corrected set value of the oxygen concentration being transmitted to a gas-metering unit and at least said one other time lag element, the gas-metering unit correcting the oxygen concentration based on said corrected set value, said at least one other time lag element determining said first response time and said second response time based on at least said corrected set value of the oxygen concentration.

8. A process in accordance with claim 7, wherein said at least one other time lag element comprises a second time lag element and a third time lag element, said second time lag element simulating the time response of the oxygen transport from the inspired air into the blood circulation, said third time lag element simulating the time response of the measuring arrangement.

9. A process in accordance with claim 7, wherein the modeling of the time response of the oxygen transport from the inspired air into the blood circulation and of the measuring method-dependent time response of the measuring arrangement used to measure the oxygen saturation is combined in the fourth process step with the simulation of the device-dependent time response in a common time response.

10. A process in accordance with claim 7, wherein the process is carried out in a continuously repeating sequence of the steps b) through h) after a first-time run of the sequence from a) to h).

11. A process in accordance with claim 7, each of said time lag elements have one or more of a first-order time function element and a time function element in a series connection.

12. A process in accordance with claim 7, wherein the set of measured oxygen saturation values is taken into account in a modeling of a patient's time response.

13. A process in accordance with claim 7, wherein a measured value of a heart rate is taken into account in a modeling of a patient's time response.

14. A process in accordance with claim 13, wherein a quality index of the set of oxygen saturation measured values and of the measured value of the heart rate are taken into account in modeling the patient's time response.

15. A process for controlling a respirator with an expiration valve, a control and calculating unit, a gas path, a gas-mixing unit, a gas-metering unit, a measuring arrangement for measuring an oxygen saturation, an input unit and a controller and a humidifying unit, the process comprising the steps of:
   a) determining a device-dependent time response of the respirator, of the gas path and of the humidifying unit and simulating said device-dependent time response in at least one first time lag element;
   b) determining a run time of a change in an oxygen concentration from a metering means in the respirator through at least said humidifying unit to the patient based on a set value and a curve of the set value of the oxygen concentration, and calculating a patient-side oxygen concentration based on said run time of said change in said oxygen concentration;
   c) performing an oxygen saturation measurement with the measuring arrangement and determining a set of measured oxygen saturation values;
   d) determining an oxygen transport time response and a measuring method-dependent time response and simulating said oxygen transport time response and said measuring method-dependent time response in at least one other time lag element, said oxygen transport time response corresponding to oxygen being transported from inspired air into a blood circulation over time, said measuring method-dependent time response being dependent upon the measuring arrangement used to measure the oxygen saturation;
   e) determining a saturation-effective oxygen concentration from the patient-side oxygen concentration and said at least one time lag element and said at least one other time lag element;
   f) forming a difference value from the set of measured oxygen saturation values and a set point of the oxygen saturation;
   g) generating a breathing gas oxygen concentration with a controller from the difference value; and
   h) linking the breathing gas oxygen concentration with the saturation-effective oxygen concentration to a corrected set value of the oxygen concentration, said corrected set value of the oxygen concentration being transmitted to a gas-metering unit and said at least one other time lag element, the gas-metering unit correcting the oxygen concentration based on said corrected set value, said at least one other time lag element determining said oxygen transport time response and said measuring method-dependent time response based on at least said corrected set value;
   continuously repeating sequence of the steps a) through h).

16. A process for controlling a respirator, the process comprising the steps of:
   providing a respirator comprising an expiration valve, a control and calculating unit, an input unit, a controller, a humidifying unit, a gas path comprising one or more feed lines and a Y-piece, a gas-mixing unit and a gas-metering unit, said Y-piece being connected to said humidifying unit and said one or more feed lines, said respirator comprising a control loop for setting an oxygen saturation corresponding to a preset set value at a patient, wherein the control loop comprises a measuring component, said measuring component comprising a measuring arrangement for measuring an oxygen saturation, said control loop comprising a modeling element, wherein said modeling element comprises a first time lag element with a device-dependent time response of said respirator and said humidifying unit;
   calculating an oxygen concentration value at the Y-piece and a saturation-effective oxygen concentration based on said device-dependent time response, wherein a change in a run time in an oxygen concentration through said one or more feed lines and said humidifying unit to said Y-piece is determined based on a set value of oxygen concentration and said device-dependent time response;
   additively linking said saturation-effective oxygen concentration with an output of said controller via a feedback and sending a summation signal as output to the gas-metering unit and to the modeling element, said summation signal comprising a new set value of oxygen concentration, wherein said new set value of oxygen concentration is provided to said modeling element as input.

17. A process in accordance with claim 16, further comprising the step of:
   respirating at least one premature or newborn child with the respirator such that damage to the eyes of the premature or newborn child and total or partial blindness of the premature or newborn child are prevented.

18. A process in accordance with claim 16, further comprising the step of:
   respirating children, youth and adults with the respirator such that hypoxic states of patients are prevented.

19. A process for controlling a respirator, the process comprising the steps of:
   providing a respirator, said respirator comprising a humidifying unit, an expiration valve, a control and calculating unit, a controller, an input unit, a gas path with at least one feed line and a Y-piece, a gas-mixing unit and a gas-metering unit, said humidifying unit being connected to said Y-piece and said at least one feed line, said control and calculating unit comprising a control loop for setting an oxygen saturation corresponding to a preset set value at a patient, wherein said control loop comprises a measuring component, said measuring component comprising an oxygen saturation sensor and an oxygen saturation-measuring unit, said control loop comprising a modeling element, wherein said modeling element comprises a first time lag element with a device-dependent time response, a second time lag element with a patient-dependent time response and a third time lag element with a time response dependent on the measuring method, said device-dependent time response comprising a device-dependent time response of at least said humidifying unit;
   calculating an oxygen concentration value at the Y-piece and a saturation-effective oxygen concentration based on said device-dependent time response, said patient-dependent time response and said measuring method-dependent time response, wherein a run time of a change in an oxygen concentration through said humidifying unit and said at least one feed line to said Y-piece is determined based on at least said device-dependent time response;
   linking the saturation-effective oxygen concentration with an output of said controller via a feedback and sending a summation signal to the gas-metering unit and to the modeling element, said summation signal comprising a corrected oxygen concentration value, said modeling element receiving said corrected oxygen concentration value and said modeling element determining one or more of said device-dependent time response, said patient-dependent time response and said time response dependent on the measuring method based on at least said corrected oxygen concentration value.

20. A process in accordance claim 19, wherein said device-dependent time response comprising a time response of said humidifying unit.

21. A process in accordance with claim 19, further comprising the step of:
respirating patients in an adverse medical care situation with the respirator.

22. A device for controlling a respirator comprising an expiration valve, a control and calculating unit, an input unit, a humidifying unit, a gas path with a Y-piece connected to the humidifying unit, a gas-mixing unit, a gas-metering unit, the device comprising:
a control loop for setting an oxygen saturation corresponding to a preset set value at a patient, wherein said control loop comprises a measuring component, said measuring component comprising a measuring arrangement for measuring an oxygen saturation, said control loop comprising a modeling element, wherein said modeling element comprises a first time lag element with a device-dependent time response of at least said humidifying unit, said control loop comprising a controller, said controller providing a controller output signal as output, wherein said modeling element is connected to said controller output signal via a feedback, said device-dependent time response and said controller output signal forming a summation signal, said summation signal being sent to the modeling element as an input variable and to the gas-metering unit as a set value of the oxygen concentration, said gas-metering unit setting an oxygen concentration in the breathing gas of patient based on said set value, said gas-metering unit determining a change in the oxygen concentration through at least said humidifying unit based on at least said device-dependent time response.

23. A device in accordance with claim 22, wherein said humidifying unit is contained in said gas path from the respirator to the patient and said modeling element includes the humidifying unit in the first time lag element with the device-dependent time response.

24. A device for controlling a respirator, the respirator comprising an expiration valve, a control and calculating unit, an input unit, a humidifying unit, a gas path with at least one feed line and a Y-piece connected to the humidifying unit, a gas-mixing unit and a gas-metering unit, the device comprising:
a control loop for setting an oxygen saturation corresponding to a preset set value at a patient, wherein said control loop comprises a measuring component, said measuring component comprising an oxygen saturation sensor and an oxygen saturation-measuring unit, said control loop comprising a modeling element and a controller, said controller providing a controller output signal as output, wherein said modeling element comprises a first time lag element with a device-dependent time response of at least said humidifying unit, a second time lag element with a patient-dependent time response and a third time lag element with a time response dependent upon a measuring method, said modeling element being connected to said controller output signal via a feedback, wherein output from said modeling element and said controller output signal form a summation signal, said summation signal being sent as an input variable to the modeling element and to the gas-metering unit as a set value of an oxygen concentration, said gas-metering unit setting an oxygen concentration in the breathing gas of patient based on said set value, said modeling element adjusting at least said device-dependent time response of said humidifying unit, said patient-dependent time response and said time response dependent upon a measuring method based on said summation signal.

25. A device in accordance with one of the claim 24, wherein each of said time lag elements have a first-order time function element and a dead time function element in a series connection.

26. A device in accordance with claim 24, wherein a set of measured oxygen saturation values is sent to the second time lag element.

27. A device in accordance with claim 26, wherein a measured value of a heart rate is sent to the second time lag element.

28. A device in accordance with one of the claim 27, wherein a quality index of the set of measured oxygen saturation values and of the measured value of the heart rate is sent to the second time lag element.

29. A device in accordance with claim 26, wherein a quality index of the set of measured oxygen saturation values is sent to the control and calculating unit and the measured value of the oxygen saturation is changed corresponding to the quality index of the set of measured values.

30. A device in accordance with claim 24, wherein said humidifying unit is arranged during inspiration in the gas path leading to the patient, wherein the humidifying unit is taken into account in the modeling element in the first time lag element.

* * * * *